US009115086B2

(12) United States Patent
Salituro et al.

(10) Patent No.: US 9,115,086 B2
(45) Date of Patent: Aug. 25, 2015

(54) THERAPEUTIC COMPOSITIONS AND RELATED METHODS OF USE

(75) Inventors: Francesco G. Salituro, Marlborough, MA (US); Jeffrey Saunders, Lincoln, MA (US)

(73) Assignee: AGIOS PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 13/339,719

(22) Filed: Dec. 29, 2011

(65) Prior Publication Data

US 2012/0165324 A1 Jun. 28, 2012

Related U.S. Application Data

(63) Continuation of application No. PCT/US2010/040485, filed on Jun. 29, 2010.

(60) Provisional application No. 61/221,406, filed on Jun. 29, 2009.

(51) Int. Cl.

| | |
|---|---|
| ***C07D 213/30*** | (2006.01) |
| ***C07D 215/36*** | (2006.01) |
| ***C07D 257/04*** | (2006.01) |
| ***C07D 263/58*** | (2006.01) |
| ***C07D 401/14*** | (2006.01) |
| ***C07D 295/26*** | (2006.01) |
| ***C07D 319/18*** | (2006.01) |
| ***A61K 31/538*** | (2006.01) |
| ***C07D 265/36*** | (2006.01) |
| ***C07D 339/06*** | (2006.01) |
| ***C07D 401/12*** | (2006.01) |

(52) U.S. Cl.

CPC ............ *C07D 215/36* (2013.01); *C07D 213/30* (2013.01); *C07D 257/04* (2013.01); *C07D 263/58* (2013.01); *C07D 265/36* (2013.01); *C07D 295/26* (2013.01); *C07D 319/18* (2013.01); *C07D 339/06* (2013.01); *C07D 401/12* (2013.01); *C07D 401/14* (2013.01)

(58) Field of Classification Search

CPC .. C07D 213/30; C07D 215/36; C07D 257/04; C07D 263/58; C07D 401/14; C07D 295/26; C07D 319/18; C07D 339/06; C07D 401/12; C07D 265/36; A61K 31/538

USPC ............... 514/230.5, 253.01, 253.07, 253.09, 514/253.12, 254.05, 255.01, 253.1; 544/360, 363, 368, 383, 366

See application file for complete search history.

(56) References Cited

U.S. PATENT DOCUMENTS

| | | | | |
|---|---|---|---|---|
| 3,046,122 | A | 7/1962 | Siis et al. | |
| 3,097,210 | A | 7/1963 | Bicking | |
| 3,998,828 | A | 12/1976 | Wiedermann | |
| 4,235,871 | A | 11/1980 | Papahadjopoulos et al. | |
| 4,315,940 | A | 2/1982 | Hitzel et al. | |
| 4,474,599 | A | 10/1984 | Rogers et al. | |
| 4,501,728 | A | 2/1985 | Geho et al. | |
| 4,593,102 | A | 6/1986 | Shanklin, Jr. | |
| 4,775,762 | A | 10/1988 | Knox et al. | |
| 4,837,028 | A | 6/1989 | Allen | |
| 4,849,424 | A | 7/1989 | Ikeda et al. | |
| 4,881,965 | A | 11/1989 | Yamamoto et al. | |
| 4,889,553 | A | 12/1989 | Rowson et al. | |
| 4,959,094 | A | 9/1990 | Wegner et al. | |
| 5,019,369 | A | 5/1991 | Presant et al. | |
| 5,122,530 | A | 6/1992 | Tomioka et al. | |
| 5,180,732 | A | 1/1993 | Tomioka et al. | |
| 5,220,028 | A | 6/1993 | Iwasawa et al. | |
| 5,252,590 | A | 10/1993 | Tomioka et al. | |
| 5,556,866 | A | 9/1996 | Aga et al. | |
| 5,834,485 | A | 11/1998 | Dyke et al. | |
| 5,843,485 | A | 12/1998 | Fernandez et al. | |
| 5,962,490 | A | 10/1999 | Chan et al. | |
| 5,965,559 | A | 10/1999 | Faull et al. | |
| 5,965,569 | A | 10/1999 | Camps Garcia et al. | |
| 6,020,357 | A | 2/2000 | Pinto et al. | |
| 6,106,849 | A | 8/2000 | Malkan et al. | |
| 6,150,356 | A | 11/2000 | Lloyd et al. | |
| 6,172,005 | B1 | 1/2001 | Selby | |
| 6,265,588 | B1 | 7/2001 | Mullner et al. | |
| 6,313,127 | B1 | 11/2001 | Waterson et al. | |
| 6,492,368 | B1 | 12/2002 | Dorsch et al. | |
| 6,511,977 | B1 | 1/2003 | Lloyd et al. | |
| 6,818,631 | B1 | 11/2004 | Nakagawa et al. | |
| 7,288,554 | B2 | 10/2007 | Finkelstein et al. | |
| 7,524,848 | B2 * | 4/2009 | Powers et al. | 514/253.01 |
| 7,572,913 | B2 | 8/2009 | McKerracher et al. | |
| 7,863,444 | B2 | 1/2011 | Calderwood et al. | |
| 8,058,313 | B2 | 11/2011 | Reddy et al. | |

(Continued)

FOREIGN PATENT DOCUMENTS

| | | | |
|---|---|---|---|
| CA | 2235621 | A1 | 5/1997 |
| CN | 101296909 | A | 10/2008 |

(Continued)

OTHER PUBLICATIONS

Tawaka et al.caplus an 1998:794998.*
VanEmelen et al, caplus an 2003:737742.*
Villoutreix et al., caplus an 2010:20993.*
Crawford et al., caplus an 2010:1218943.*
Wong et al., 2013, http://www.hindawi.com/journals/ijcb/2013/242513/.*
Ge et al. "*Anaplasma phagocytophilum* inhibits human neutrophil apoptosis via upregulation of bfl-1, maintenance of mitochondrial membrane potential and prevention of caspase 3 activation." Cellular Microbiology, 2005, 7(1 ), 29-38.
International Search Report dated Apr. 4, 2012 for related Application PCT/US2011/065633.
International Search Report dated May 3, 2012 for related application PCT/US2011/066595.
International Search Report for PCT/US2010/059778 dated Mar. 17, 2011.
Supplemental EP Search Report & Written Opinion for EP 10 79 4667 dated Jan. 15, 2013.

(Continued)

*Primary Examiner* — Sun Jae Yoo
(74) *Attorney, Agent, or Firm* — Lando & Anastasi LLP

(57) ABSTRACT

Compositions comprising compounds that modulate pyruvate kinase M2 (PKM2) are described herein. Also described herein are methods of using the compounds that modulate PKM2 in the treatment of cancer.

27 Claims, No Drawings

(56) References Cited

U.S. PATENT DOCUMENTS

| | | | | |
|---|---|---|---|---|
| 2003/0082877 | A1 | 5/2003 | Ootsuka et al. | |
| 2003/0095958 | A1 | 5/2003 | Bhisetti et al. | |
| 2003/0106381 | A1 | 6/2003 | Krouth et al. | |
| 2003/0158232 | A1 | 8/2003 | Cheng et al. | |
| 2003/0187001 | A1 | 10/2003 | Calderwood et al. | |
| 2003/0207882 | A1 | 11/2003 | Stocker et al. | |
| 2004/0048283 | A1 | 3/2004 | Pau et al. | |
| 2004/0152648 | A1 | 8/2004 | Ullrich et al. | |
| 2004/0198979 | A1 | 10/2004 | Dhanak et al. | |
| 2004/0235755 | A1 | 11/2004 | Eigenbrodt et al. | |
| 2005/0176675 | A1 | 8/2005 | Gorny | |
| 2007/0032418 | A1 | 2/2007 | Shapiro et al. | |
| 2007/0127505 | A1 | 6/2007 | Laurila et al. | |
| 2007/0280918 | A1 | 12/2007 | Schwartz et al. | |
| 2008/0004269 | A1 | 1/2008 | Xu et al. | |
| 2008/0021116 | A1 | 1/2008 | Ullrich et al. | |
| 2008/0044833 | A1 | 2/2008 | Connors | |
| 2008/0051414 | A1 | 2/2008 | Hurley et al. | |
| 2009/0048227 | A1 | 2/2009 | Chakravarty et al. | |
| 2009/0054453 | A1 | 2/2009 | Alcaraz et al. | |
| 2009/0163545 | A1 | 6/2009 | Goldfarb | |
| 2009/0247499 | A1* | 10/2009 | Fletcher et al. .......... | 514/210.02 |
| 2009/0270454 | A1 | 10/2009 | Weingarten et al. | |
| 2010/0105657 | A1 | 4/2010 | Nordvall et al. | |
| 2010/0179150 | A1 | 7/2010 | Basarab et al. | |
| 2010/0331307 | A1 | 12/2010 | Salituro et al. | |
| 2011/0046083 | A1 | 2/2011 | Cantley et al. | |
| 2011/0224252 | A1 | 9/2011 | Dumeunier et al. | |
| 2011/0312931 | A1 | 12/2011 | Cioffi et al. | |

FOREIGN PATENT DOCUMENTS

| | | | |
|---|---|---|---|
| DE | 3813886 | A1 | 11/1989 |
| DE | 19841985 | A1 | 3/2000 |
| EP | 0246749 | A2 | 11/1987 |
| EP | 0628551 | A1 | 12/1994 |
| EP | 1586558 | A2 | 10/2005 |
| FR | 2735127 | A1 | 12/1996 |
| GB | 1274436 | A | 5/1972 |
| IT | 1176770 | B | 8/1987 |
| JP | S61129129 | A | 6/1986 |
| JP | 06-025177 | | 2/1994 |
| JP | 2002-193710 | A | 7/2002 |
| JP | 2007/238458 | A | 9/2007 |
| WO | 8501289 | A1 | 3/1985 |
| WO | 9211761 | A1 | 7/1992 |
| WO | 93/13072 | A1 | 7/1993 |
| WO | 97/28129 | A1 | 8/1997 |
| WO | 97/28141 | A1 | 8/1997 |
| WO | 98/03350 | A1 | 1/1998 |
| WO | 99/16751 | A1 | 4/1999 |
| WO | 0017202 | A1 | 3/2000 |
| WO | 00/53596 | A2 | 9/2000 |
| WO | 01/07440 | A1 | 2/2001 |
| WO | 02/072077 | A2 | 9/2002 |
| WO | 02/095063 | A1 | 11/2002 |
| WO | 03022277 | A1 | 3/2003 |
| WO | 03037252 | A2 | 5/2003 |
| WO | 03/062235 | A1 | 7/2003 |
| WO | 03/073999 | A2 | 9/2003 |
| WO | 03/076422 | A1 | 9/2003 |
| WO | 03093297 | A2 | 11/2003 |
| WO | 2004/004730 | A2 | 1/2004 |
| WO | 2004014851 | A2 | 2/2004 |
| WO | 2004/037251 | A1 | 5/2004 |
| WO | 2004/073619 | A2 | 9/2004 |
| WO | 2004/074438 | A2 | 9/2004 |
| WO | 2004/110375 | A2 | 12/2004 |
| WO | 2005/072642 | A1 | 8/2005 |
| WO | 2005/117591 | A2 | 12/2005 |
| WO | 2006/004195 | A1 | 1/2006 |
| WO | 2006/016062 | A1 | 2/2006 |
| WO | 2006033628 | A1 | 3/2006 |
| WO | 2006-038594 | A1 | 4/2006 |
| WO | 2006043950 | A1 | 4/2006 |
| WO | 2006052190 | A1 | 5/2006 |
| WO | 2006070198 | A1 | 7/2006 |
| WO | 2006/122546 | A1 | 11/2006 |
| WO | 2006117762 | A2 | 11/2006 |
| WO | 2007023186 | A1 | 3/2007 |
| WO | 2007/127505 | A2 | 11/2007 |
| WO | 2008/019139 | A2 | 2/2008 |
| WO | 2008/026658 | A1 | 3/2008 |
| WO | 2008047198 | A1 | 4/2008 |
| WO | 2008/050168 | A1 | 5/2008 |
| WO | 2009012430 | A1 | 1/2009 |
| WO | 2009013126 | A1 | 1/2009 |
| WO | 2009/025781 | A1 | 2/2009 |
| WO | 2009/053102 | A1 | 4/2009 |
| WO | 2010/042867 | A2 | 4/2010 |
| WO | 2010/105243 | A1 | 9/2010 |
| WO | 2010118063 | A2 | 10/2010 |
| WO | 2010/129596 | A1 | 11/2010 |
| WO | 2011002817 | A1 | 1/2011 |
| WO | 2011/072174 | A1 | 6/2011 |
| WO | 2011137089 | A1 | 11/2011 |
| WO | 2012/092442 | A1 | 7/2012 |

OTHER PUBLICATIONS

Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.

Klapars et al., "A General and Efficient Copper Catalyst for the Amidation of Aryl Halides and the N-Arylation of Nitrogen Heterocycles," J. Am. Chem. Soc., 123 (31), 7727-7729 (2001).

Kumar et al., "In vivo factors influencing tumour M2-pyruvate kinase level in human pancreatic cancer cell lines." Tumour Biol.;31(2):69-77 (2010).

Lee et al., "An Efficient Synthesis of 2,8-Diazabicyclo[4.3.0]-Nonane Derivatives Via Intramolecular Cyclization Reaction," Synth. Comm., 25 (23), 3741-3746 (1995).

Lee, "Consolidation Effect of Phenylalanine-administration of Antitumor Activity of a 5 Fluorouracil," Med. J. Kagoshima Univ. 37(3-4): 285-308 (1985).

Lee, et al., "Pyruvate kinase isozyme type M2 (PKM2) interacts and cooperates with Oct-4 in regulating transcription" International J. Biochem. & Cell Biol., vol. 40, # 5,2008, 1043-1054.

Li et al., "Quantitative proteome analysis of multidrug resistance in human ovarian cancer cell line." J Cell Biochem.;109(4):625-33 (2010).

Li et al., "Screening and identification of interactive proteins of SH2D4A." Yi Chuan.;32(7):712-8 (2010). (Abstract Only).

Mass, R. D., "The HER receptor family: a rich target for therapeutic development", Int. J. Radiation Oncology Bio. Phys. vol. 58(3): 932-940, 2004.

Oeda, "On some 2,5-Dialikl-piperazines," Bull. Chem. Soc., 13, 465-470 (1938).

Park, "Prevention of type 2 diabetes mellitus from the viewpoint of genetics." Diabetes Research and Clinical Practice 2004; 66S: S33-S35.

Paudler et al., "3,7-Disubstituted octahydro-1,5-diazocines. Their conversion into tetrahydro-1 ,5-diazocines and into ring-contracted products," J. Org. Chern., 32 (8), 2425-2430 (1967).

Pollard et al., "Some Amides of Piperazines," J. Am. Chem. Soc., 75 (2), 491 (1953).

Pujol, et. al., "Is there a case for cisplatin in the treatment of smallcell lung cancer? A meta-analysis of randomized trials of a cisplatin-containing regimen versus a regimen without this alkylating agent" British Journal of Cancer, Cancer Research Campaign, vol. 83, issue 1, pp. 8-15, 2000.

Remington's, "Structure Activity Relationship and Drug Design," Pharmaceutical Sciences, pp. 420-425p. 420-425, 1980.

Rich, et. al., "Development of novel targeted therapies in the treatment of malignant glioma" Nature Rev. Drug Disc., Nature Publishing Group, vol. 3, pp. 430-446, 2004.

Root et al., "Genome-Scale Loss-of-Function Screening with a Lentiviral RNAi Library," Nat Methods 3: 715-719 (2006).

(56) References Cited

OTHER PUBLICATIONS

Ruan et al., "HSP60, a protein downregulated by IGFBP7 in colorectal carcinoma." J Exp Clin Cancer Res.;29:41 (2010).
Sabatine et al., "Metabolomic Identification of Novel Biomarkers of Myocardial Ischemia," Circulation 112: 3868-3875 (2005).
Schneider, et. al., "Tumor M2-pyruvate kinase in the follow-up of inoperable lung cancer patients: a pilot study." Cancer Letters, Elsevier, vol. 193, pp. 91-98, 2003.
Schroth et al., "RingschluBreaktion von Diacetylen mit Diaminen: Eine Ciniache von 2,3-Dihydro-1 ,4-diazepinen," Zeitschritt Fur Chemie., 6 (4), 143 (1969).
Seibel et al., "Synthesis and evaluation of B-lactams (piperazones) as elastase inhibitors," Bioorg. Med. Chern. Ltrs., 13 (3),387-389 (2003).
Shi, et al., "Silencing of pkm2 increases the efficacy of docetaxel in human lung cancer xenografts in mice." Cancer Science, vol. 101, # 6, 1447-1453, Jun. 2010.
Stewart et al., "Piperazines. I. Derivatives of Piperazine-1-Carboxylic and -1,4-Dicarboxylic Acid," J. Org. Chern., 18 (1),1478-1483 (1953).
Supplementary Search Report for EP10794668 Mailed Oct. 18, 2012.
Surh, "Cancer Chemoprevention with Dietary Phytochemicals", Nature Reviews Cancer, Nature Publishing Group, vol. 3, p. 768-780, 2003.
Szoka et al., "Comparative properties and methods of preparation of lipid vesicles (liposomes )," Ann. Rev. Biophys. Bioeng., 9, 467-508 (1980).
Uozumi et al., "Catalytic asymmetric construction of morpholines and piperazines by palladium-catalyzed tandem allylic substitution reactions," J. Org. Chem., 58 (24),6826-6832 (1993).
Vander Heiden et al., "Growth Factors Can Influence Cell Growth and Survival Through Effects on Glucose Metabolism," Mol Cell Bioi. 21: 5899-5912 (2001).
Vander Heiden et al., "Identification of Small Molecule Inhibitors of Pyruvate Kinase M2," Biochemical Pharmacology. 79(8): 1118-1124 (2010).
Villen et al., "Large-Scale Phosphorylation Analysis of Mouse Liver," Proc Nat! Acad Sci USA 104: 1488-1493 (2007).
Written Opinion of the International Searching Authority for PCT/US2008/009828, dated Dec. 5, 2008.
Yamada and Noguchi, "Nutrient and Hormonal Regulation of Pyruvate Kinase Gene Expression," Biochem J. 337: 1-11 (1999).
Yar et al., "An Annulation Reaction for the Synthesis of Morpholines, Thiomorpholines, and Piperazines from !3-Heteroatom Amino Compounds and Vinyl Sulfonium Salts," Angewandte Chemie., 47 (20),3784-3786 (2008).
Adveenko, et al., "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3 (2009), 408-416.
Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970, pp. 850-853.
Behun et al., "The Chemistry of Pyrazine and Its Derivatives. IV. The Alkylation and Arylation of Methylpyrazine," J Org. Chern., 26 (9),3379-3382 (1961).
Benesch et al., "The clinicopathological and prognostic relevance of pyruvate kinase M2 and pAkt expression in breast cancer." Anticancer Res.;30(5):1689-94 (2010).
Berger, et. al., "Treatment of Pancreatic Cancer: Challenge of the Facts" World J. Surg., Societe Internationale de Chirurgie, vol. 27, pp. 1075-1083, 2003.
Bonuccelli et al., "The reverse Warburg effect: Glycolysis inhibitors prevent the tumor promoting effects of caveolin-1 deficient cancer associated fibroblasts." Cell Cycle.;9(10) (2010).
Boxer, et al., "Evaluation of Substituted N,N?-Diarylsulfonamides as Activators of the Tumor Cell Specific M2 Isoform of Pyruvate Kinase", J Med Chem. Feb. 11, 2010; 53(3): 1048.
Boxer, et al., "Identification of activators for the M2 isoform of human pyruvate kinase Version 3", Sep. 2009, Probe Reports from the NIH Molecular Libraries Program [Internet]. Bethesda (MD): National Center for Biotechnology Information (US).
Budinger et al., "Cellular Energy Utilization and Supply During Hypoxia in Embryonic Cardiac Myocytes," Am J Physiol. 270: L44-53 (1996).
Buschow et al., "MHC class II-associated proteins in B-cell exosomes and potential functional implications for exosome biogenesis." Immunol Cell Biol. (2010).
Cecil Textbook of Medicine, edited by Bennet, J.C., and Plum F., 20th edition, vol. 1, 1004-1010, 1996.
Chabner, et. al., "Chemotherapy and the war on cancer", Nature Rev. Cancer, Nature Publishing Group, vol. 5, pp. 65-72, 2005.
Chan et al., "Synthesis and characterization of poly(amide sulfonamide)s (PASAs)," J Polymer. Sci., 33 (15), 2525-2531 (1995).
Christofk et al., "Pyruvate Kinase M2 is a Phosphotyrosine-Binding Protein," Nature 452: 181-186 (2008).
Christofk et al. , "The M2 Splice Isoform of Pyruvate Kinase is Important for Cancer Metabolism and Tumour Growth," Nature 452: 230-233 (2008).
Clement, et. al., "Production of Intracellular Superoxide Mediates Dithiothreitol-Dependent Inhibition of Apoptotic Cell Death" Antioxidants and Redox Signaling, Mary Ann Liebert, vol. 7, issues 3-4, pp. 456-464, 2005.
Cohen et al., "The development and therapeutic potential of protein kinase inhibitors", Current Opinion in Chemical Biology, 3,459-465, 1999.
Cuzick, et. al., "Overview of the main outcomes in breast-cancer prevention trials" The Lancet, The Lancet Publishing Group, vol. 361, pp. 296-300, 2003.
Database Chemcats, Chemical Abstracts Service, Columbus, OH, US "Bionet Screening Compounds" Key Organics Ltd., Camelford, Cornwall (2001).
Dermer et al., "Another Anniversary for the War on Cancer", Bio/Technology, 1994, 12:320.
Dombrauckas, et al., Structural Basis for Tumor Pyruvate Kinasa M2 Allosteric Regulation and Catalysis, Biochemistry, vol. 44, p. 9717-9429 (2005).
Eigenbrodt et al., "Double Role for Pyruvate Kinase Type M2 in the Expansion of Phosphometabolite Pools Found in Tumor Cells," Crit Rev Oncog. 3: 91-115 (1992). (Abstract only).
Engelman et al., "Allelic Dilution Obscures Detection of a Biologically Significant Resistance Mutation in EGFR-Amplified Lung Cancer," J Clin Invest 116: 2695-2706 (2006).
Eswaran et al., "Crystal Structures and Inhibitor Identification for PTPN5, PTPRR and PTPN7: A Family of Human MAPK-Specific Protein Tyrosine Phosphatases," Biochem J. 395: 483-491 (2006).
Extended European Search Report (European Application No. 07836571.5), Dated Sep. 29, 2010.
Fabbro et al. "Protein kinases as targets for anticancer agents: from inhibitors to useful drugs." Pharmacology & Therapeutics 93, 79-98, 2002.
Freshney et al.,Culture of Animal Cells, A Manual of Basic Technique, Alan R. Liss, Inc., 1983, New York, p. 4.
Friedman et al., "Leptin and the regulation of body weight in mammals" Nature. vol. 395, 1996.
Golub et al., "Molecular Classification of Cancer: Class Discovery and Class Prediction by Gene Expression Monitoring", Science, 286, 531-537, 1999.
Gupta et al., "Dominant negative mutations affect oligomerisation of human pyruvate kinase M2 isozyme and promote cellular growth and polyploidy." J Biol Chem. (2010).
Hitosugi T et al: "Tyrosine Phosphorylation Inhibits PKM2 to Promote the Warburg Effect and Tumor Growth" Science Signaling, American Association for the Advancement of Science, US LNKD-DOI:10.1126/SCISIGNAL.2000431, vol. 2, No. 97, Nov. 17, 2009, pp. RA73-1.
Hulleman, et al., "Pyruvate kinase M2 and prednisolone resistance in acute lymphoblastic leukemia." Haematologica. Sep. 2009; 94(9): 1322-1324.

(56) References Cited

OTHER PUBLICATIONS

Inglese et al., "Quantitative high-throughput screening: A titration-based approach that efficiently identifies biological activities in large chemical libraries," Proc. Natl. Acad. Sci., 103 (31), 11473-11478 (2006).
International Preliminary Report on patentability for International Application No. PCT/US2007/017519, mailed Jul. 8, 2008.
International Preliminary Report on Patentability for PCT/US2008/009828, dated Feb. 16, 2010.
International Preliminary Report on Patentability, Application No. PCT/US2009/060237, dated Apr. 12, 2011.
International Search Report & Written Opinion for PCT/US10/030139 dated Dec. 10, 2010.
International Search Report & Written Opinion for PCT/US10/40485 dated Aug. 11, 2010.
International Search Report and the Written Opinion of the International Search Authority (PCT/US07/17519), mailed Jul. 8, 2008.
International Search Report dated Mar. 5, 2012 for related international application No. PCT/US2011/067752.
International Search Report for PCT/US10/040486 dated Sep. 1, 2010.
International Search Report for PCT/US2008/009828, dated Dec. 5, 2008.
International Search Report for PCT/US2010/033610 dated Jul. 22, 2010.
International Search Report, Application No. PCT/US2009/060237, dated Jun. 16, 2010.
International Search Report, Application No. PCT/US2011/033852, dated Aug. 3, 2011.
Jiang et al., "Evaluation of thieno[3,2-b]pyrrole[3,2-djpyridazinones as activators of the tumor cell specific M2 isoform of pyruvate kinase." Bioorg. Med. Chern. Lett., 20 (11), 3387-3393 (2010).
Joshi et al., "Age-related faecal calprotectin, lactoferrin and tumour M2-PK concentrations in healthy volunteers." Ann Clin Biochem. ;47(Pt 3):259-63 (2010).
Jurica et al., "The Allosteric Regulation of Pyruvate Kinase by Fructose-1 ,6-Bisphosphate," Structure 6: 195-210 (1998).
Kao et al., "A Small-Molecule Inhibitor of the Ribonucleolytic Activity of Human Angiogenin That Possesses Antitumor Activity," Proc. Natl. Acad. Sci. USA, 99(15): 10066-10071 (2002).
Kharalkar et al., "Identification of Novel Allosteric Regulators of Human-Erythrocyte Pyruvate Kinase," Chem Biodivers. 4: 2603-2617 (2007).
European Search report for EP Application No. 10 794 667.5 dated Oct. 9, 2013.
International Search Report for PCT/US2011/065633 dated Jun. 18, 2013.
Komoriya et al. "Design, synthesis, and biological activity of non-basic compounds as factor Xa inhibitors: SAR study of S1 and aryl binding sites" Bioorganic & Medicinal Chemistry 13 No. 12 (2005) 3927-3954.
Patel et al. "Synthesis of some new idolinone derivatives containing piperazine moiety" Bulgarian Chemical Communications, 2003 Bol 35 No. 4 pp. 242-244.
Proisy et al. "Rapid Synthesis of 3-Aminoisoquinoline-5-sulfonamides Using the Buchwald-Hartwig Reaction" Synthesis 2009, No. 4, pp. 561-566.
Furuya et al., Inactivation of the 3-phosphoglycerate dehydrogenase gene in mice: changes in gene expression and associated regulatory networks resulting from serine deficiency. Funct Integr Genomics (2008) 8:235-249.
International Preliminary Report for related application No. PCT/US2011/067752 dated Apr. 11, 2013.
International Preliminary Report on Patentability for PCT/US2010/040489 dated Jan. 12, 2012.
International Search Report for Application No. PCT/US12/60099 dated Jan. 8, 2013.
Kung et al. "Small Molecule Activation of PKM2 in Cancer Cells Induces Serine Auxotrophy" Chemistry & Biology, 19, 1187-1198, Sep. 21, 2012.
STN File CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3[[4-[(2,5-dimethoxyphenyl)methyl]-1-piperazinyl]carbonyl]-N-(4-methoxyphenyl)-4-methyl-".
STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
Web posting, Pyruvate kinase M2 isozyme (PKM2), SciBX 5(42), Published online Oct. 25, 2012, Abstract only.
Ye et al., Pyruvate kinase M2 promotes de novo serine synthesis to sustain mTORC1 activity and cell proliferation, PNAS 109(18), 2012, pp. 6904-6909.
Steiner et al. "Synthesis and Antihypertensive Activity of New 6-Heteroaryl-3-hydrazinopyridazine Derivatives" Journal of Medicinal Chemistry (1981) vol. 24, No. 1, pp. 59-63.
Conti et al. "Su alcuni analoghi assigenati della benzo-tiazine 2-3-diidro-3-cheto-benzo-1-4-ossazine 6-sostitute" Bollettino Scientifico Della Facolta Di Chimica Industriale Di Bologna (1957) vol. XV, No. 2, pp. 33-36.
European Search Report for European Application No. 11808773.3 dated Apr. 9, 2014.
European Search Report for European Application No. 11811257.2 dated Apr. 23, 2014.
STN File CA, Registry No. 321433-63-0, entered STN on Feb. 12, 2001, Chemical Abstracts Index Name "1H-Pyrrole-2-sulfonamide, 1-[3-chloro-5-(trifluoromethyl)-2-pyridinyl]-N-phenyl" Available though Key Organics (under the BIONET brand) Jan. 1994.
STN File CA, Registry No. 321433-64-1, entered STN on Feb. 12, 2001, Chemical Abstracts Index Name "1H-Pyrrole-2-sulfonamide, 1-[3-chloro-5-(trifluoromethyl)-2-pyridinyl]-N-(4-methphenyl)" Available though Key Organics (under the BIONET brand) Jan. 1994.
STN File CA, Registry No. 321433-65-2, entered STN on Feb. 12, 2001, Chemical Abstracts Index Name "1H-Pyrrole-2-sulfonamide, 1-[3-chloro-5-(trifluoromethyl)-2-pyridinyl]-N-(3,5-dimethylphenyl)" Available though Key Organics (under the BIONET brand) Jan. 1994.
STN File CA, Registry No. 321433-66-3, entered STN on Feb. 12, 2001, Chemical Abstracts Index Name "1H-Pyrrole-2-sulfonamide, 1-[3-chloro-5-(trifluoromethyl)-2-pyridinyl]-N-(4-methoxyphenyl)" Available though Key Organics (under the BIONET brand) Jan. 1994.
STN File CA, Registry No. 321433-68-5, entered STN on Feb. 12, 2001, Chemical Abstracts Index Name "1H-Pyrrole-2-sulfonamide, 1-[3-chloro-5-(trifluoromethyl)-2-pyridinyl]-N-propyl" Available though Key Organics (under the BIONET brand) Jan. 1994.
STN File CA, Registry No. 321433-69-6, entered STN on Feb. 12, 2001, Chemical Abstracts Index Name "1H-Pyrrole-2-sulfonamide, 1-[3-chloro-5-(trifluoromethyl)-2-pyridinyl]-N-(2-methoxyethyl)" Available though Key Organics (under the BIONET brand) Jan. 1994.
STN File CA, Registry No. 338397-92-5, entered STN on May 25, 2001, Chemical Abstracts Index Name "1H-Pyrrole-2-sulfonamide, 1-[3-chloro-5-(trifluoromethyl)-2-pyridinyl]-N,N-dimethyl" Available though Key Organics (under the BIONET brand) Feb. 1993.
STN File CA, Registry No. 338397-95-8, entered STN on May 25, 2001, Chemical Abstracts Index Name "1H-Pyrrole-2-sulfonamide, N-[(4-chlorophenyl)-1-[3-chloro-5-(trifluoromethyl)-2-pyridinyl]" Available though Key Organics (under the BIONET brand) Feb. 1993.
STN File CA, Registry No. 338397-96-9, entered STN on May 25, 2001, Chemical Abstracts Index Name "1H-Pyrrole-2-sulfonic acid,

(56) References Cited

OTHER PUBLICATIONS

1-[3-chloro-5-(trifluoromethyl)-2-pyridinyl]-4-chlorophenyl ester" Available though Key Organics (under the BIONET brand) Feb. 1993.

STN File CA, Registry No. 338406-58-9, entered STN on May 25, 2001, Chemical Abstracts Index Name "1H-Pyrrole-2-sulfonamide, 1-[3-chloro-5-(trifluoromethyl)-2-pyridinyl]-N-[2-(trifluoromethyl)phenyl]" Available though Key Organics (under the BIONET brand) Mar. 1993.

STN File CA, Registry No. 338406-64-7, entered STN on May 25, 2001, Chemical Abstracts Index Name "1H-Pyrrole-2-sulfonamide, 1-[3-chloro-5-(trifluoromethyl)-2-pyridinyl]-N-(3-pyridinylmethyl)" Available though Key Organics (under the BIONET brand) Mar. 1993.

STN File CA, Registry No. 338406-72-7, entered STN on May 25, 2001, Chemical Abstracts Index Name "1H-Pyrrole-2-sulfonamide, N-[(4-chlorophenyl)methyl]-1-[3-chloro-5-(trifluoromethyl)-2-pyridinyl]" Available though Key Organics (under the BIONET brand) Mar. 1993.

STN File CA, Registry No. 338407-11-7, entered STN on May 25, 2001, Chemical Abstracts Index Name "1H=Pyrrole-2-sulfonamide, 1-[3-chloro-5-(trifluoromethyl)-2-pyridinyl]-N-[3-chloro-4-[[5-(trifluoromethyl)-2-pyridinyl]oxy]phenyl]" Available though Key Organics (under the BIONET brand) Mar. 1993.

STN File CA, Registry No. 338407-13-9, entered STN on May 25, 2001, Chemical Abstracts Index Name "Benzoic acid, 3-[[[1-[3-chloro-5-(trifluoromethyl)-2-pyridinyl]-1H-pyrrol-2-yl]sulfonyl]amino]" Available though Key Organics (under the BIONET brand) Mar. 1993.

Supplemental EP Search Report for European Application No. 10714131.9 dated Oct. 17, 2014.

* cited by examiner

THERAPEUTIC COMPOSITIONS AND RELATED METHODS OF USE

CLAIM OF PRIORITY

The present application is a continuation of International Application No. PCT/US2010/040485, filed Jun. 29, 2010, published as International Publication No. WO 2011/002816 on Jan. 6, 2011, which claims priority from U.S. Ser. No. 61/221,406, filed Jun. 29, 2009, each of which is incorporated herein by reference in its entirety.

BACKGROUND OF INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Thus, the modulation of PKM2 may be effective in the treatment of, e.g., obesity, diabetes, autoimmune conditions, and proliferation-dependent diseases, e.g., benign prostatic hyperplasia (BPH). Current modulators of pyruvate kinase are not selective, making it difficult to treat disease related to pyruvate kinase function.

Furthermore, phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 (i.e., activators of PKM2) can also inhibit the growth and proliferation of cancer cells, activated immune cells, and fat cells.

There is a continuing need for novel treatments of diseases such as cancer, diabetes, obesity, autoimmune conditions, proliferation-dependent diseases (e.g., BPH), and other diseases related to the function of pyruvate kinase (e.g., PKM2).

SUMMARY OF INVENTION

Described herein are compounds that modulate pyruvate kinase M2 (PKM2) and pharmaceutically acceptable salts, solvates, and hydrates thereof, for example, compounds that activate PKM2. Provided are compositions and pharmaceutical kits comprising a compound of this invention and the use of such compositions and kits in methods of treating diseases and conditions that are related to pyruvate kinase function (e.g., PKM2 function), including, e.g., cancer, diabetes, obesity, autoimmune disorders, and benign prostatic hyperplasia (BPH).

In one aspect, the invention features a pharmaceutical composition comprising a compound of formula (I) or a pharmaceutically acceptable salt thereof:

(I)

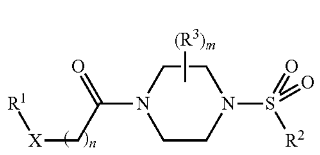

wherein:

m is 0, 1 or 2;

n is 0, 1 or 2;

X is O, S, $NR^b$, alkylenyl, cycloalkylenyl, or a bond;

$R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl;

$R^2$ is an optionally substituted aryl or an optionally substituted heteroaryl;

each $R^3$ is independently selected from halo, alkyl, haloalkyl and —$OR^a$;

each $R^a$ is independently selected from alkyl, haloalkyl and optionally substituted heteroaryl; and each $R^b$ is independently hydrogen or alkyl.

In another aspect, provided is a method of treating or preventing a disorder (e.g., treating) described herein (e.g., cancer) comprising administering to a subject a compound of formula (I), where m, n, X, $R^1$, $R^2$, $R^3$, $R^a$, and $R^b$ are as defined above.

In another aspect, provided is a method of modulating (e.g., increasing) the level of PKM2 activity and/or glycolysis (e.g., modulating the endogenous ability of a cell in the patient to down regulate PKM2) in a patient in need thereof. The method comprises the step of administering an effective amount of a compound described herein to the patient in need thereof, thereby modulating (e.g., increasing) the level of PKM2 activity and/or glycolysis in the patient. In some embodiments, a compound or a composition described herein is used to maintain PKM2 in its active conformation or activate pyruvate kinase activity in proliferating cells as a means to divert glucose metabolites into catabolic rather than anabolic processes in the patient.

In another aspect, provided is a method of inhibiting cell proliferation in a patient in need thereof. The method comprises the step of administering an effective amount of a compound described herein to the patient in need thereof, thereby inhibiting cell proliferation in the patient. E.g., this method can inhibit growth of a transformed cell, e.g., a cancer cell, or generally inhibit growth in a PKM2-dependent cell that undergoes aerobic glycolysis.

In another aspect, the invention features a method of treating a patient suffering from or susceptible to a disease or disorder associated with the function of PKM2 in a patient in need thereof. The method comprises the step of administering an effective amount of a compound described herein to the patient in need thereof, thereby treating, preventing or ameliorating the disease or disorder in the patient. In another embodiment the modulator is provided in a pharmaceutical composition.

In another embodiment the method includes identifying or selecting a patient who would benefit from modulation (e.g., activation) of PKM2. E.g., the patient can be identified on the basis of the level of PKM2 activity in a cell of the patient for treatment of cancer associated with PKM2 function. In another embodiment the selected patient is a patient suffering from or susceptible to a disorder or disease identified herein, e.g., a disorder characterized by unwanted cell growth or proliferation, e.g., cancer, obesity, diabetes, atherosclerosis, restenosis, and autoimmune diseases.

In another embodiment the compound described herein is administered at a dosage and frequency sufficient to increase lactate production or oxidative phosphorylation.

DETAILED DESCRIPTION

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups. The terms "heteroarylalkyl" or "heteroaralkyl" refer to an alkyl moiety in which an alkyl hydrogen atom is replaced by a heteroaryl group. Heteroaralkyl includes groups in which more than one hydrogen atom is replaced by a heteroaryl group. Examples or "heteroarylalkyl" or "heteroaralkyl" include methyl-3-pyridyl and methyl-2-pyridyl.

The term "alkylene" refers to a divalent alkyl, e.g., $—CH_2—$, $—CH_2CH_2—$, and $—CH_2CH_2CH_2—$.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively. The term "aralkylamino" refers to a —NH(aralkyl) radical. The term alkylaminoalkyl refers to a (alkyl)NH-alkyl-radical; the term dialkylaminoalkyl refers to a (alkyl)$_2$N-alkyl-radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes saturated cyclic, bicyclic, tricyclic, or polycyclic hydrocarbon groups having 3 to 12 carbons. Any substitutable ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl. The term "cycloalkylenyl" refers to a divalent cycloalkyl.

The terms "heterocyclyl" or "heterocyclic group" refer to 3- to 14-membered non-aromatic ring structures (e.g., 3- to 10-membered rings, more preferably 3- to 7-membered rings), whose ring structures include one to four heteroatoms independently selected from O, N and S. The heterocyclyl or heterocyclic groups can contain fused or spiro rings. Heterocycles can also be polycycles, with each group having, e.g., 5-7 ring members. The term "heterocyclyl" or "heterocyclic group" includes saturated and partially saturated heterocyclyl structures. The term "heteroaryl" refers to a 5-14 membered (i.e., a 5-8 membered monocyclic, 8-12 membered bicyclic, or 11-14 membered tricyclic) aromatic ring system having 1-3 ring heteroatoms if monocyclic, 1-6 ring heteroatoms if bicyclic, or 1-9 ring heteroatoms if tricyclic, said ring heteroatoms independently selected from O, N, and S (e.g., 1-3, 1-6, or 1-9 ring heteroatoms of N, O, or S if monocyclic, bicyclic, or tricyclic, respectively). Any substitutable ring atom can be substituted (e.g., by one or more substituents). Heterocyclyl and heteroaryl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic or heteroaryl ring can be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, $—CF_3$, —CN, or the like.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any substitutable ring atom can be substituted (e.g., by one or more substituents). The cycloalkenyl groups can contain fused or spiro rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, or S (e.g., 1-3, 1-6, or 1-9 ring heteroatoms of N, O, or S if monocyclic, bicyclic, or tricyclic, respectively). The unsaturated carbon or the heteroatom may optionally be the point of attachment of the heterocycloalkenyl substituent. Any substitutable ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The terms "hetaralkyl" and "heteroaralkyl", as used herein, refers to an alkyl group substituted with a heteroaryl group. The ring heteroatoms of the compounds provided herein may be in the form of N—O, S(O), or $S(O)_2$.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, alkoxycarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group "substituted" on an alkyl, cycloalkyl, alkenyl, alkynyl, heterocyclyl, heterocycloalkenyl, cycloalkenyl, aryl, or heteroaryl group at any substitutable atom of that group. Any substitutable atom can be substituted. Unless otherwise specified, such substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C═S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "selective" is meant at least 2-fold, 3-fold, 4-fold, 5-fold, 6-fold, or 10-fold greater modulation (e.g., activation) of PKM2 than PKM1. The term "activator" as used herein means an agent that (measurably) increases the activity of a pyruvate kinase (e.g., PKM2) or causes pyruvate kinase (e.g., PKM2) activity to increase to a level that is greater than PKM2's basal levels of activity. For example, the activator may mimic the effect caused by a natural ligand (e.g., FBP). The activator effect caused by a compound provided herein may be to the same, or to a greater, or to a lesser extent than the activating effect caused by a natural ligand, but the same type of effect is caused. A compound provided herein can be evaluated to determine if it is an activator by measuring either directly or indirectly the activity of the pyruvate kinase when subjected to said compound. The activity of a compound provided herein can be measured, for example, against a control substance. In some instances, the activity measured of the test compound is for activation of PKM2. The activity of PKM2 can be measured, for example, by monitoring the concentration of a substrate such as ATP or NADH.

Compounds

Described herein are compounds and compositions that modulate PKM2, for example, activate PKM2. Compounds that modulate PKM2, e.g., activate PKM2, can be used to treat disorders such as neoplastic disorders (e.g., cancer) or fat related disorders (e.g., obesity). Exemplary compounds include the compounds of Formula I (I)

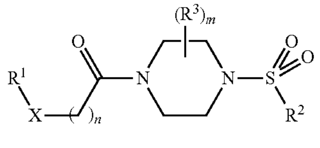

described herein.

In some embodiments, $R^1$ is an optionally substituted alkyl (e.g., methyl or t-butyl). In some embodiments, $R^1$ is optionally substituted cycloalkyl (e.g., cyclopentyl or cyclohexyl).

In some embodiments, $R^1$ is aryl (e.g., monocyclic aryl or bicyclic aryl). In some embodiments, $R^1$ is an optionally substituted monocyclic aralkyl (e.g., benzyl or methylpyridyl). In some embodiments, $R^1$ is an optionally substituted phenyl. In some embodiments, $R^1$ is an optionally substituted naphthyl. In some embodiments, $R^1$ is phenyl. In some embodiments, $R^1$ is naphthyl.

In some embodiments, $R^1$ is heteroaryl (e.g., monocyclic N-containing heteroaryl or bicyclic N-containing heteroaryl). In some embodiments, $R^1$ is an optionally substituted monocyclic 5-8 membered heteroaryl (e.g., pyridyl, pyrimidyl, pyrazyl, oxazolyl, thiazolyl, triazolyl or imidazolyl). In some embodiments, $R^1$ is an optionally substituted 6-12 membered bicyclic heteroaryl (e.g., quinolyl). In some embodiments, $R^1$ is optionally substituted pyridyl (e.g., 2-pyridyl, 3-pyridyl or 4-pyridyl). In some embodiments, $R^1$ is optionally substituted pyrimidyl (e.g., 2-pyridinyl). In some embodiments, $R^1$ is optionally substituted pyrazyl (e.g., 2-pyrazyl). In some embodiments, $R^1$ is optionally substituted oxazolyl (e.g., 4-oxazolyl). In some embodiments, $R^1$ is optionally substituted thiazolyl (e.g., 4-thiazolyl). In some embodiments, $R^1$ is optionally substituted imidazolyl (e.g., 4-imidazolyl). In some embodiments, $R^1$ is optionally substituted triazolyl (e.g., 4-triazolyl).

In some embodiments, m is 0.

In some embodiments, n is 0. In some embodiments, X is oxygen (O). In some embodiments, $R^1$ is optionally substituted straight or branched $C_{1-6}$ alkyl (e.g., methyl, ethyl, isopropyl or t-butyl). In some embodiments, $R^1$ is optionally substituted benzyl. In some embodiments, $R^1$ is optionally substituted methyl-3-pyridyl). In some embodiments, X is a bond. In some embodiments, $R^1$ is optionally substituted cyclohexyl. In some embodiments, $R^1$ is optionally substituted phenyl. In some embodiments, X is cycloalkylenyl (e.g., cyclopropylenyl). In some embodiments, $R^1$ is optionally substituted phenyl (e.g., phenyl or 4-trifluorophenyl).

In some embodiments, n is 1. In some embodiments, X is oxygen (O). In some embodiments, $R^1$ is optionally substituted phenyl (e.g., phenyl, 4-methylphenyl, 4-methoxycarbonylphenyl, 4-fluorophenyl or 2,4-dichlorophenyl). In some embodiments, $R^1$ is optionally substituted pyridyl (e.g., 3-pyridyl). In some embodiments, $R^1$ is phenyl optionally substituted with heteroaryl (e.g., 4-tetrazolylphenyl). In some embodiments, $R^1$ is optionally substituted benzyl. In some embodiments, X is $NR^b$. In some embodiments, $R^b$ is hydrogen (H). In some embodiments, $R^1$ is optionally substituted alkyl (e.g., methyl). In some embodiments, $R^1$ is optionally substituted phenyl. In some embodiments, X is a bond. In some embodiments, $R^1$ is optionally substituted phenyl (e.g., 2,5-bis(trifluoromethyl)phenyl or 4-trifluoromethylphenyl). In some embodiments, $R^1$ is optionally substituted cyclopropyl. In some embodiments, X is sulfur (S). In some embodiments, $R^1$ is optionally substituted phenyl (e.g., phenyl or 4-methylphenyl).

In some embodiments, n is 2. In some embodiments, X is a bond. In some embodiments, $R^1$ is optionally substituted phenyl (e.g., phenyl or 4-trifluoromethylphenyl).

In some embodiments, $R^2$ is aryl (e.g., monocyclic aryl or bicyclic aryl). In some embodiments, $R^2$ is optionally substituted phenyl. In some embodiments, $R^2$ is optionally substituted naphthyl. In some embodiments, $R^2$ is naphthyl (1-naphthyl or 2-naphthyl).

In some embodiments, $R^2$ is optionally substituted heteroaryl (e.g., monocyclic N-containing heteroaryl or bicyclic N-containing heteroaryl). In some embodiments, $R^2$ is an optionally substituted 5-8 membered monocyclic heteroaryl (e.g., pyridyl, pyrimidyl, or pyrrolyl). In some embodiments, $R^2$ is an optionally substituted 6-12 membered bicyclic heteroaryl (e.g., quinolyl, isoquinolyl, quinazolinyl, quinaxolinyl, cinnolinyl, indolyl, benzoxazolyl, pyrrolopyridyl, benzimidazolyl, or benzthiazolyl). In some embodiments, $R^2$ is optionally substituted pyridyl (e.g., 2-pyridyl, 3-pyridyl or 4-pyridyl). In some embodiments, $R^2$ is optionally substituted pyrimidyl (e.g., 2-pyrimidyl). In some embodiments, $R^2$ is optionally substituted quinolyl (e.g., 8-quinolyl). In some embodiments, $R^2$ is optionally substituted isoquinolyl. In some embodiments, $R^2$ is optionally substituted quinazolinyl (e.g., 2-quinazolinyl or 7-quinazolinyl). In some embodiments, $R^2$ is optionally substituted quinoxalinyl (e.g., 2-quinoxalinyl, 6-quinoxalinyl). In some embodiments, $R^2$ is optionally substituted cinnolinyl (e.g., 7-cinnolyl). In some embodiments, $R^2$ is optionally substituted indolyl (e.g., 6-indolyl). In some embodiments, $R^2$ is optionally substituted benzoxazolyl (e.g., 5-benzoxazolyl, 6-benzoxazolyl). In some embodiments, $R^2$ is optionally substituted pyrrolopyridyl (e.g., 5-pyrrolopyridyl). In some embodiments, $R^2$ is optionally substituted benzimidazolyl (e.g., 6-benzimidazolyl). In some embodiments, $R^2$ is optionally substituted benzthiazolyl (e.g, 5-benzthiazolyl, 6-benzthiazolyl).

In some embodiments, $R^2$ is an unsubstituted napthyl. In some embodiments, $R^2$ is an optionally substituted phenyl. In some embodiments, $R^2$ is phenyl substituted with halo (e.g., 3,5-dichlorophenyl, 2,6-difluorophenyl or 4-fluorophenyl). In some embodiments, $R^2$ is phenyl substituted with halo alkyl (e.g., 3-trifluoromethylphenyl). In some embodiments, $R^2$ is phenyl disubstituted with halo alkyl (e.g., 3,5-bis(trifluoromethyl)phenyl). In some embodiments, $R^2$ is phenyl substituted with one halo and one alkoxy (e.g., 2-methoxy-5-chlorophenyl). In some embodiments, $R^2$ is phenyl substituted with one haloalkyl and one halo (e.g., 3-bromo-5-trifluoromethylphenyl). In some embodiments, $R^2$ is phenyl substituted with one haloalkyl and one cycloalkyl (e.g, 3-cyclopropyl-5-trifluoromethylphenyl). In some embodiments, $R^2$ is phenyl substituted with one haloalkyl and one acyl group (e.g., 3-trifluoromethyl-5-methoxycarbonylphenyl). In some embodiments, $R^2$ is disubstituted phenyl, wherein the two substituents, when taken together with the carbon atoms to which they are attached, form an optionally substituted ring. In some embodiments, $R^2$ is disubstituted phenyl, wherein the two substituents, taken together with the carbon atoms to which they are attached, form a 5-6 membered heterocyclic ring. In some embodiments, $R^2$ is disubstituted phenyl, wherein the two substituents, taken together with the carbon atoms to which they are attached, form the following structure:

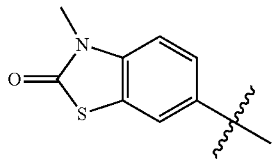 [SMILES: *c1ccc2c(c1)sc(=O)n2C]

In some embodiments, $R^2$ is disubstituted phenyl, wherein the two substituents, taken together with the carbon atoms to which they are attached, form the following structure:

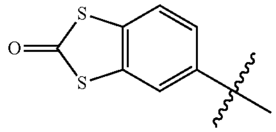 [SMILES: *c1ccc2sc(=O)sc2c1]

In some embodiments, $R^2$ is disubstituted phenyl, wherein the two substituents, taken together with the carbon atoms to which they are attached, form the following structure:

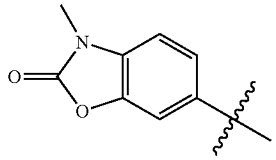 [SMILES: *c1ccc2c(c1)oc(=O)n2C]

In some embodiments, $R^2$ is disubstituted phenyl, wherein the two substituents, taken together with the carbon atoms to which they are attached, form the following structure:

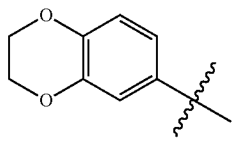 [SMILES: *c1ccc2c(c1)OCCO2]

In some embodiments, $R^2$ is an optionally substituted pyrrolyl. In some embodiments, $R^2$ is pyrrolyl substituted with an optionally substituted pyrimidyl (e.g., 3-trifluoromethyl-6-chloro-2-pyridimidyl).

In some embodiments, $R^2$ is an N-containing monocyclic heteroaryl, m is 0, n is 1, X is O and $R^1$ is optionally substituted aryl.

In some embodiments, provided is a compound of formula (II) or a pharmaceutically acceptable salt thereof:

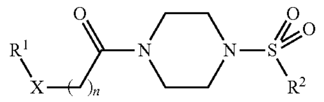

(II)

wherein:

n is 0, 1 or 2;

X is O, S, $NR^b$, or cycloalkylenyl;

$R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl; provided that when n is 0 and X is O, then $R^1$ is selected from optionally substituted aryl, optionally substituted heteroaryl, optionally substituted heterocyclyl, optionally substituted cycloalkyl, an optionally substituted aralkyl, or optionally substituted heteroaralkyl;

$R^2$ is a bicyclic heteroaryl; and each $R^b$ is independently hydrogen or alkyl.

In some embodiments (e.g., of formula I, II, II-a, III or IV), $R^b$ is H, $CH_3$ or $CH_2CH_3$. In some embodiments (e.g., of formula I, II, II-a, III or IV), cycloalkylenyl is cyclopropylenyl.

In some embodiments, provided is a compound of formula (II-a) or a pharmaceutically acceptable salt thereof:

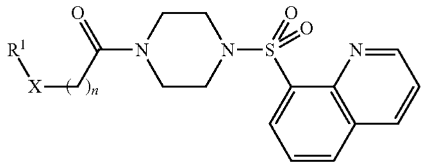

(II-a)

where n, X, $R^1$ and $R^b$ are as defined in formula (II).

In some embodiments, provided is a compound of formula (III) or a pharmaceutically acceptable salt thereof:

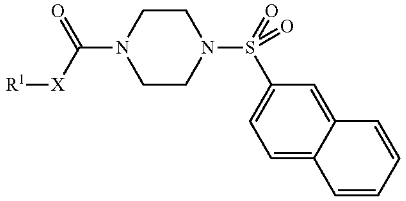

(III)

wherein:

when X is S, $NR^b$, or cycloalkylenyl, $R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl;

when X is O, $R^1$ is selected from an optionally substituted aralkyl, or optionally substituted heteroaralkyl; and each $R^b$ is independently hydrogen or alkyl.

In some embodiments, provided is a compound of formula (IV) or a pharmaceutically acceptable salt thereof:

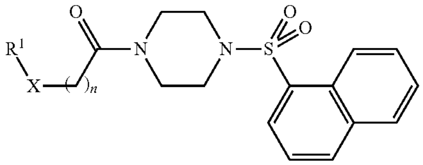

(IV)

wherein:

when n is 0, X is S, $NR^b$, or cycloalkylenyl;

when n is 1 or 2, X is O, X is S, $NR^b$, or cycloalkylenyl;

$R^1$ is selected from optionally substituted alkyl, optionally substituted aryl, optionally substituted heteroaryl, optionally substituted heterocyclyl, optionally substituted cycloalkyl, an optionally substituted aralkyl, or optionally substituted heteroaralkyl; and each $R^b$ is independently hydrogen or alkyl.

In some embodiments, a compound described herein modulates PKM2 by interacting (e.g., binding) with the FBP binding pocket. For example, a compound described herein can compete with FBP binding in PKM2.

In some embodiments a compound described herein has one or more properties described herein, e.g., one or more of the following properties: it is an allosteric modulator (e.g., activator); it modulates the release of FBP (e.g., promotes); it is a modulator (e.g., agonist) of FBP, e.g., an agonist which binds with a lower, about the same, or higher affinity than does FBP; it modulates (e.g., promotes) the dissolution of tetrameric PKM2; it modulates (e.g., promotes) the assembly of tetrameric PKM2; it selectively modulates (e.g., activates) PKM2 over at least one other isoform of PK, e.g., it is selective for PKM2 over PKR, PKM1, or PKL; is has an affinity for PKM2 which is greater than its affinity for at least one other isoform of PK, e.g., PKR, PKM1, or PKL.

In another embodiment the activator of PKM2 utilized in the methods and compositions of this invention operates by or has one or more of the following mechanisms or properties:

a. it is an allosteric activator of PKM2;

b. it modulates (e.g., stabilizes) the binding of FBP in a binding pocket of PKM2;

c. it modulates (e.g., promotes) the release of FBP from a binding pocket of PKM2;

d. it is a modulator (e.g., an agonist), e.g., an analog, of FBP, e.g., an agonist which binds PKM2 with a lower, about the same, or higher affinity than does FBP;

e. it modulates (e.g., promotes) the dissolution of tetrameric PKM2;

f. it modulates (e.g., promotes) the assembly of tetrameric PKM2;

g. it modulates (e.g., stabilizes) the tetrameric conformation of PKM2;

h. it modulates (e.g., promotes) the binding of a phosphotyrosine containing polypeptide to PKM2;

i. it modulates (e.g., promotes) the ability of a phosphotyrosine containing polypeptide to induce release of FBP from PKM2, e.g., by inducing a change in the conformation of PKM2, e.g., in the position of Lys 433, thereby hindering the release of FBP;

k. it binds to or changes the position of Lys 433 relative to the FBP binding pocket;

l. it selectively modulates (e.g., activates) PKM2 over at least one other isoform of PK, e.g., it is selective for PKM2 over one or more of PKR, PKM1, or PKL;

m. it has an affinity for PKM2 which is greater than its affinity for at least one other isoform of PK, e.g., PKR, PKM1, or PKL.

A compound described herein may be an activator of PKM2. Exemplary compounds are shown in Table 1. As shown in Table 1, A refers to an activator of PKM2 with an $EC_{50}$<10 μM. B refers to an activator of PKM2 with an $EC_{50}$ between 10 μM and 100 μM. C refers to an activator of PKM2 with an $EC_{50}$ greater than 100 μM.

TABLE 1

| Compound | $EC_{50}$ |
|---|---|
| 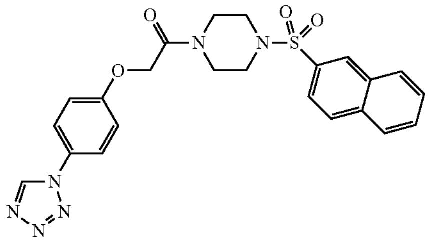 [SMILES: O=C(COc1ccc(-n2cnnn2)cc1)N1CCN(S(=O)(=O)c2ccc3ccccc3c2)CC1] | A |
| 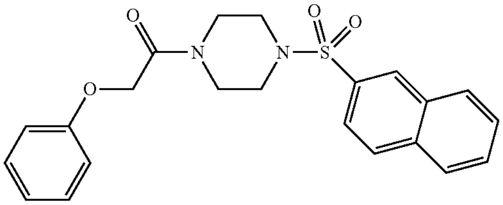 [SMILES: O=C(COc1ccccc1)N1CCN(S(=O)(=O)c2ccc3ccccc3c2)CC1] | A |
| 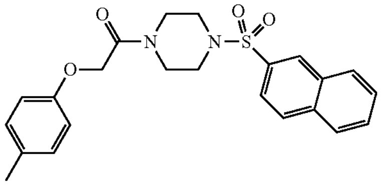 [SMILES: Cc1ccc(OCC(=O)N2CCN(S(=O)(=O)c3ccc4ccccc4c3)CC2)cc1] | A |
| 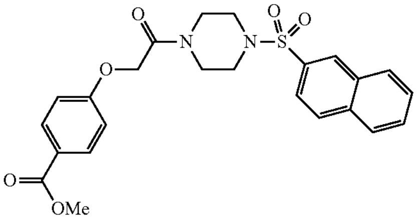 [SMILES: COC(=O)c1ccc(OCC(=O)N2CCN(S(=O)(=O)c3ccc4ccccc4c3)CC2)cc1] | A |
| 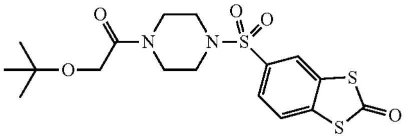 [SMILES: CC(C)(C)OCC(=O)N1CCN(S(=O)(=O)c2ccc3sc(=O)sc3c2)CC1] | B |
| 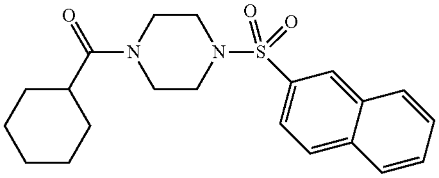 [SMILES: O=C(C1CCCCC1)N1CCN(S(=O)(=O)c2ccc3ccccc3c2)CC1] | A |

TABLE 1-continued

| Compound | $EC_{50}$ |
|---|---|
| 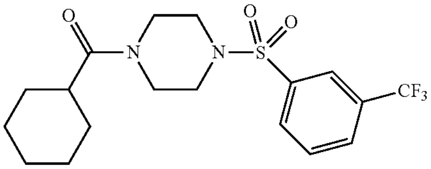 [SMILES: O=C(C1CCCCC1)N1CCN(S(=O)(=O)c2cccc(C(F)(F)F)c2)CC1] | A |
| 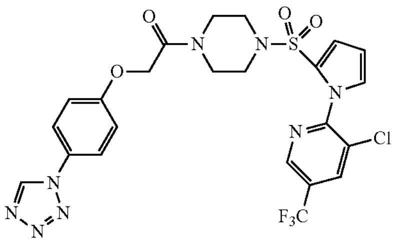 [SMILES: O=C(COc1ccc(-n2cnnn2)cc1)N1CCN(S(=O)(=O)c2cccn2-c2ncc(C(F)(F)F)cc2Cl)CC1] | B |
| 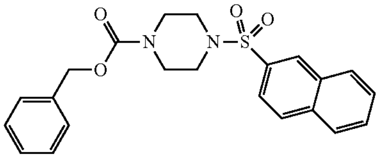 | A |
| 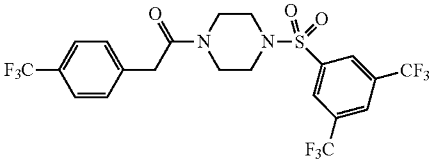 [SMILES: O=C(Cc1ccc(C(F)(F)F)cc1)N1CCN(S(=O)(=O)c2cc(C(F)(F)F)cc(C(F)(F)F)c2)CC1] | C |
| 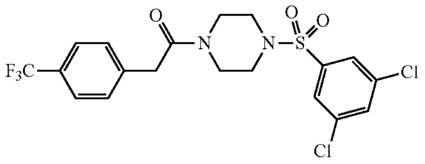 [SMILES: O=C(Cc1ccc(C(F)(F)F)cc1)N1CCN(S(=O)(=O)c2cc(Cl)cc(Cl)c2)CC1] | B |
| 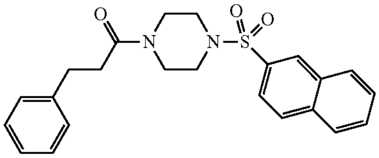 [SMILES: O=C(CCc1ccccc1)N1CCN(S(=O)(=O)c2ccc3ccccc3c2)CC1] | A |
| 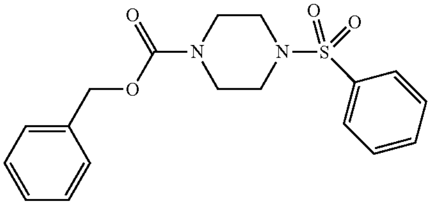 [SMILES: O=C(OCc1ccccc1)N1CCN(S(=O)(=O)c2ccccc2)CC1] | A |
| 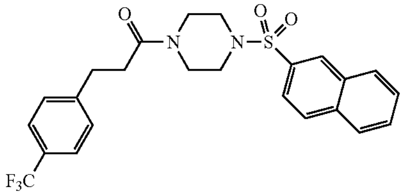 [SMILES: O=C(CCc1ccc(C(F)(F)F)cc1)N1CCN(S(=O)(=O)c2ccc3ccccc3c2)CC1] | A |

TABLE 1-continued
| Compound | $EC_{50}$ |
| --- | --- |
| 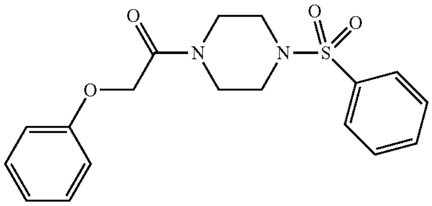 [SMILES: O=C(COc1ccccc1)N1CCN(S(=O)(=O)c2ccccc2)CC1] | A |
| 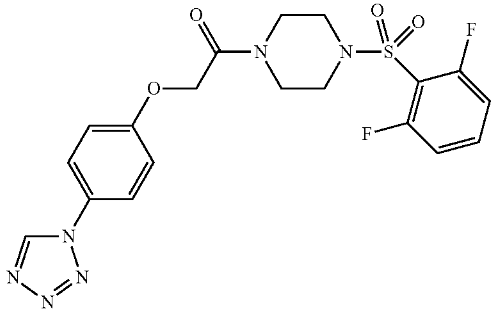 [SMILES: O=C(COc1ccc(-n2cnnn2)cc1)N1CCN(S(=O)(=O)c2c(F)cccc2F)CC1] | A |
| 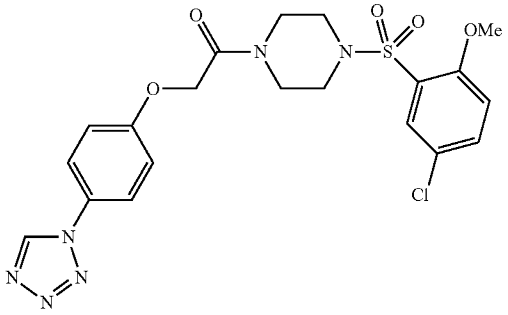 [SMILES: COc1ccc(Cl)cc1S(=O)(=O)N1CCN(C(=O)COc2ccc(-n3cnnn3)cc2)CC1] | B |
| 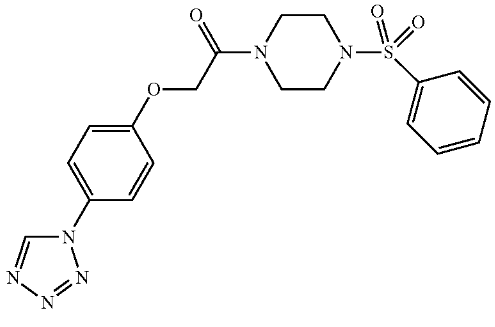 [SMILES: O=C(COc1ccc(-n2cnnn2)cc1)N1CCN(S(=O)(=O)c2ccccc2)CC1] | A |
| 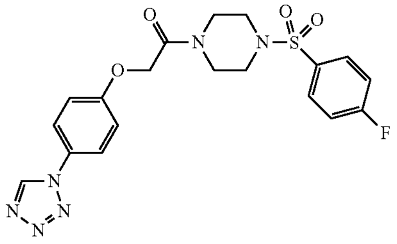 [SMILES: O=C(COc1ccc(-n2cnnn2)cc1)N1CCN(S(=O)(=O)c2ccc(F)cc2)CC1] | A |
TABLE 1-continued
| Compound | $EC_{50}$ |
| --- | --- |
| 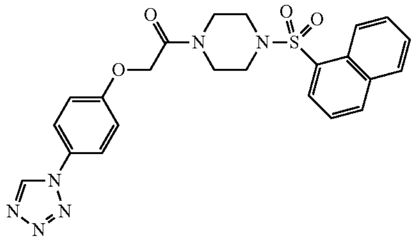 [SMILES: O=C(COc1ccc(-n2cnnn2)cc1)N1CCN(S(=O)(=O)c2cccc3ccccc23)CC1] | A |
| 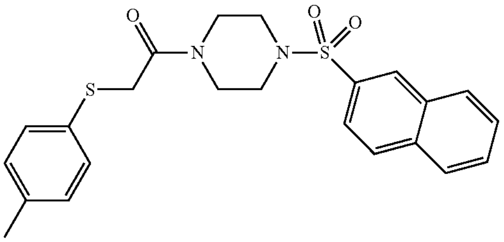 [SMILES: Cc1ccc(SCC(=O)N2CCN(S(=O)(=O)c3ccc4ccccc4c3)CC2)cc1] | A |
| 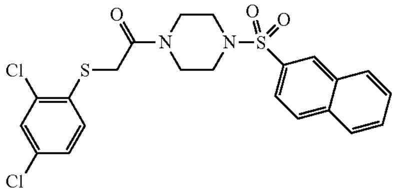 [SMILES: O=C(CSc1ccc(Cl)cc1Cl)N1CCN(S(=O)(=O)c2ccc3ccccc3c2)CC1] | A |
| 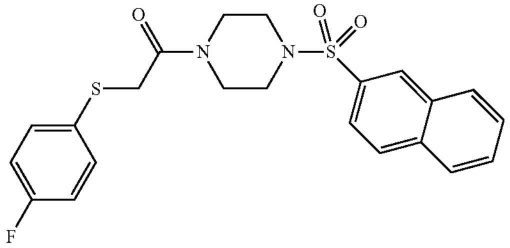 [SMILES: O=C(CSc1ccc(F)cc1)N1CCN(S(=O)(=O)c2ccc3ccccc3c2)CC1] | A |
| 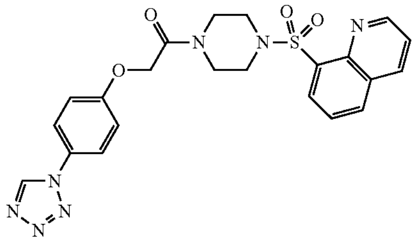 [SMILES: O=C(COc1ccc(-n2cnnn2)cc1)N1CCN(S(=O)(=O)c2cccc3cccnc23)CC1] | B |
| 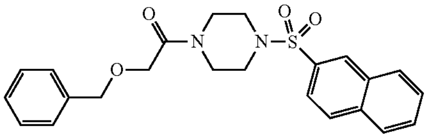 [SMILES: O=C(COCc1ccccc1)N1CCN(S(=O)(=O)c2ccc3ccccc3c2)CC1] | A |
| 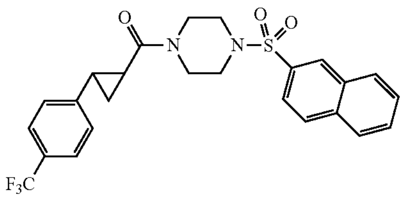 [SMILES: O=C(C1CC1c1ccc(C(F)(F)F)cc1)N1CCN(S(=O)(=O)c2ccc3ccccc3c2)CC1] | A |

TABLE 1-continued
| Compound | $EC_{50}$ |
|---|---|
| 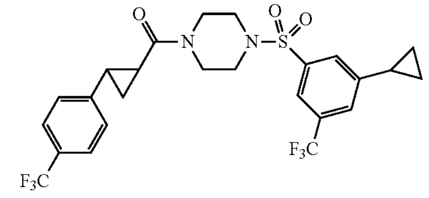 [SMILES: O=C(C1CC1c1ccc(C(F)(F)F)cc1)N1CCN(S(=O)(=O)c2cc(C3CC3)cc(C(F)(F)F)c2)CC1] | A |
| 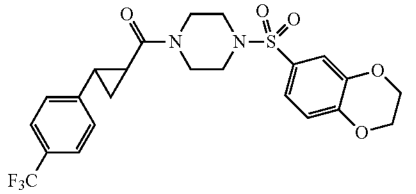 [SMILES: O=C(C1CC1c1ccc(C(F)(F)F)cc1)N1CCN(S(=O)(=O)c2ccc3c(c2)OCCO3)CC1] | A |
| 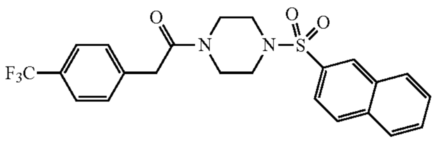 [SMILES: O=C(Cc1ccc(C(F)(F)F)cc1)N1CCN(S(=O)(=O)c2ccc3ccccc3c2)CC1] | A |
| 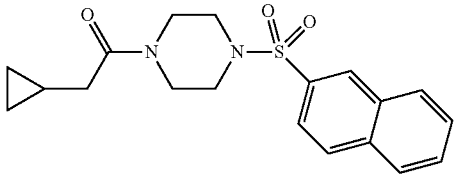 [SMILES: O=C(CC1CC1)N1CCN(S(=O)(=O)c2ccc3ccccc3c2)CC1] | A |
| 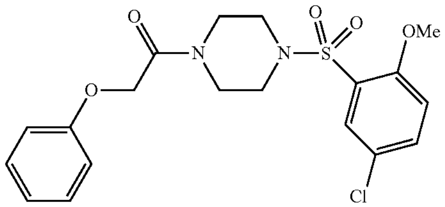 [SMILES: COc1ccc(Cl)cc1S(=O)(=O)N1CCN(C(=O)COc2ccccc2)CC1] | C |
| 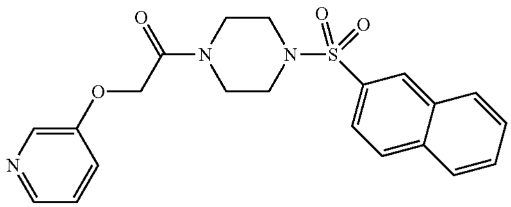 [SMILES: O=C(COc1cccnc1)N1CCN(S(=O)(=O)c2ccc3ccccc3c2)CC1] | A |
| 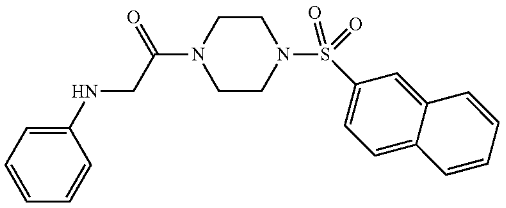 | A |
TABLE 1-continued
| Compound | $EC_{50}$ |
|---|---|
| 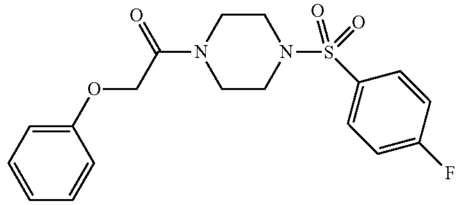 [SMILES: O=C(COc1ccccc1)N1CCN(S(=O)(=O)c2ccc(F)cc2)CC1] | A |
| 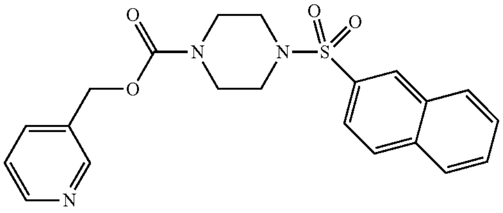 [SMILES: O=C(OCc1cccnc1)N1CCN(S(=O)(=O)c2ccc3ccccc3c2)CC1] | A |
| 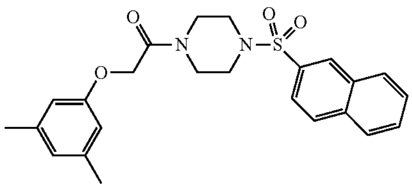 [SMILES: Cc1cc(C)cc(OCC(=O)N2CCN(S(=O)(=O)c3ccc4ccccc4c3)CC2)c1] | A |
| 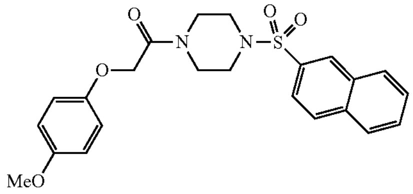 [SMILES: COc1ccc(OCC(=O)N2CCN(S(=O)(=O)c3ccc4ccccc4c3)CC2)cc1] | A |
| 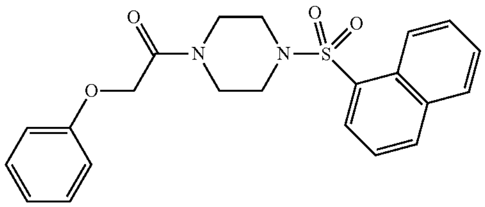 [SMILES: O=C(COc1ccccc1)N1CCN(S(=O)(=O)c2cccc3ccccc23)CC1] | A |
| 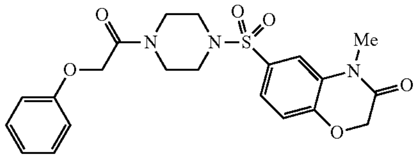 [SMILES: CN1C(=O)COc2ccc(S(=O)(=O)N3CCN(C(=O)COc4ccccc4)CC3)cc21] | B |
| 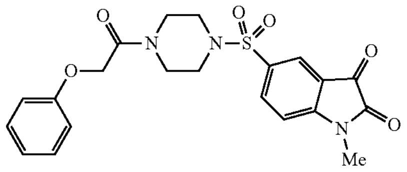 [SMILES: CN1C(=O)C(=O)c2cc(S(=O)(=O)N3CCN(C(=O)COc4ccccc4)CC3)ccc21] | B |
| 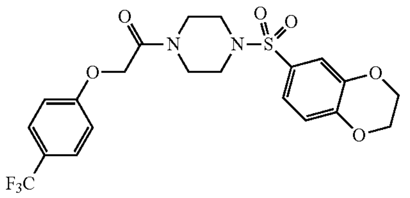 [SMILES: O=C(COc1ccc(C(F)(F)F)cc1)N1CCN(S(=O)(=O)c2ccc3c(c2)OCCO3)CC1] | C |

TABLE 1-continued

| Compound | $EC_{50}$ |
| --- | --- |
| 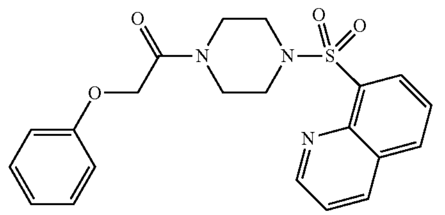 [SMILES: O=C(COc1ccccc1)N1CCN(S(=O)(=O)c2cccc3cccnc23)CC1] | A |
| 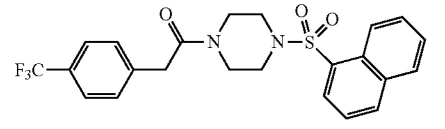 [SMILES: O=C(Cc1ccc(C(F)(F)F)cc1)N1CCN(S(=O)(=O)c2cccc3ccccc23)CC1] | A |

The compounds described herein can be made using a variety of synthetic techniques.

Scheme 1.

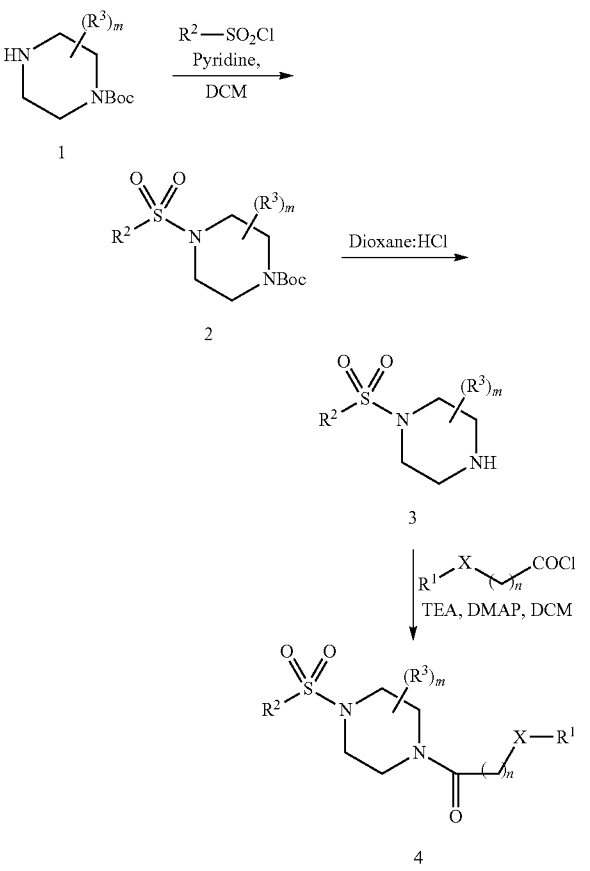

$R^1$, $R^2$, $R^3$, m and n = as defined herein

Scheme 1 above is an exemplary synthetic sequence that depicts a representative synthesis of certain compounds described herein. Boc-protected piperazine 1 is reacted with the appropriate sulfonyl chloride under standard coupling conditions to provide moiety 2. Deprotection of the Boc group in 2 is accomplished by reaction under acidic conditions to provide piperazine 3. Coupling of 3 with the appropriate acid chloride under standard coupling conditions subsequently provided target molecule 4.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention.

The compounds provided herein (e.g. of Formula I) may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds of this invention may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio*., (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Methods of Evaluating Compounds

The compounds described herein can be evaluated for ability to modulate PKM2 (e.g., activate PKM2) by methods known in the art. In some embodiments, compounds described herein are evaluated for ability to modulate PKM2 (e.g. activate PKM2) in serine deficient conditions. In some embodiments, exemplary methods include contacting the compound with a cell-based assay which allows assessment of the ability to modulate (e.g., activate) PKM2. E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate PKM2). The evaluation could also include measuring a change in pyruvate or a determination of an alteration in mitochondrial membrane potential, e.g., as measured by fluorescent potentiometric dyes.

The activity of the PKM enzyme measured in the screening assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 2.

TABLE 2

| Component of Reaction Condition | Amount in Activation Assay |
|---|---|
| ADP | 0.1-5.0 mM |
| Phosphoenolpyruvate | 0.1-5.0 mM |
| NADH | 10-1000 μM |
| Lactate dehydrogenase | 0.1-10 units |
| Fructose-1,6-bisphosphate | 0 |
| DTT | 0.1-50 mM |
| Brij 35 | 0.01-1% |
| Glycerol | 0.1-10% |
| Pyruvate Kinase M2 (used for screen) | 1-100 pg |
| DMSO | 1-10% |

In some embodiments, a compound such as a compound described herein, can be evaluated in a cellular/ex vivo assay. For example, a cell is treated with a compound described herein (i.e., a PKM2 activator), and the compound is evaluated, for example for its ability to enter the cell and bind to PKM2, inducing an activated conformation of PKM2. The excess unbound compound can then be washed away with PBS, and the cells lysed, for example, by snap-freezing on dry ice, followed by addition of a detergent-containing lysis buffer. The lysate, in which activated PKM2 remains intact, can then be removed and added to a chemical cocktail including the chemicals necessary to measure pyruvate kinase activity. The assay can be coupled to another assay such as an assay that is coupled to the LDHa enzyme. The amount of pyruvate kinase activity that is measured can then be normalized to the total protein content in the lysate, and related to the concentration of PKM2 activator that was added to the cell. This can allow an $AC_{50}$ (concentration at which PKM2 is activated 50%) value to be derived. The total fold-increase in activity over mock-treated cells can also be calculated, and the "maximum level of activation" can be used to distinguish between compounds that fully activate PKM2 and compounds that can only partially activate PKM2. In the case of measuring PKM2 activity from tissue (for example, in a cell tumor), animals harboring the tissue/tumor of interest can be dosed with a compound. After a specified period of time in which exposure has been achieved in the target tissue/tumor of interest, the tissue/tumor can then be harvested from the animal, snapfrozen, and then lysed and homogenized. The amount of pyruvate kinase activity in this lysate can then be quantitated as described above.

PKM1 and PKM2 for use in the screening/testing methods described herein may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., *E. coli*) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

Activator compounds useful as PKM2 activators are those demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, specific compounds can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Methods of Treatment

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Other exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia;

Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Cancer Combination Therapies

In some embodiments, a compound described herein is administered together with an additional cancer treatment. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g. a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can modulate PKM2. Accordingly, a patient and/or subject can be selected for treatment using a compound described herein by first evaluating the patient and/or subject to determine whether the subject is in need of modulation of PKM2, and if the subject is determined to be in need of modulation of PKM2, then optionally administering to the subject a compound described herein.

A subject can be evaluated as being in need of modulation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor). In some embodiments, the patient is evaluated using a radiological assay or evaluation of hemolytic parameters.

EXAMPLES

Example 1

PKM2 Assay

Procedure:

- PKM2 stock enzyme solution was diluted in Reaction Buffer
- 2 μL of compound was added into each well first, and then 180 μL of the Reaction Mix was added.
- Reaction mixture with compound (without ADP) were incubated for 30 minutes at 4° C.
- Plates were re-equilibrated to room temperature prior to adding 20 μL ADP to initiate the reaction.
- Reaction progress was measured as changes in absorbance at 340 nm wavelength at room temperature (25° C.)

Reaction Mix: PKM2 (50 ng/well), ADP (0.7 mM), PEP (0.15 mM), NADH (180 μM), LDH (2 units) in Reaction Buffer Reaction Buffer: 100 mM KCl, 50 mM Tris pH 7.5, 5 mM $MgCl_2$, 1 mM DTT, 0.03% BSA.

Example 2

Compounds and Synthesis

Scheme 2:

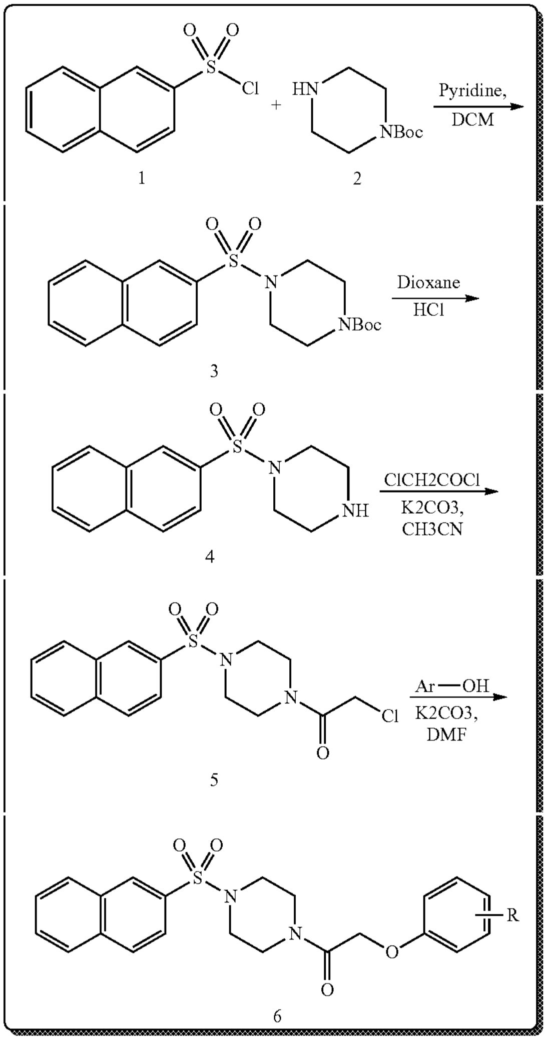

1 2 3 4 5 6

Procedure for Compound 3:

In a two neck round bottom flask, tert-butyl-piperazine-1-carboxylate (2) (0.0145 moles, 2.71 g, 1.1 eq) and 2-naphthalene sulfonyl chloride (1) (0.0132 moles, 3.0 g, 1 eq) were charged in DCM (40 mL). Triethyl amine (0.0396 moles, 4.01 g, 3.0 eq) was added slowly at room temperature. The resulting mixture was stirred for 3 h at room temperature. After completion of the reaction, dilute HCl was added (10 mL) and extracted with DCM (2×20 mL). The combined organic layers were washed with water (15 mL) and brine solution (1×20 mL). The resulting organic layer was dried over anhydrous $Na_2SO_4$ and concentrated under reduced pressure. The crude product (3) was obtained as a white solid (4.5 g, 90.36%) which was taken forward to the next step without purification.

Procedure for Compound 4:

In a two neck round bottom flask compound 3 (tert-butyl-4-(2-(4-(naphthalene-2-ylsulfonyl) piperazine-1-carboxylate (0.0119 moles, 4.5 g, 1 eq)) was taken in 1,4-dioxane saturated with HCl (30 mL). The resulting mixture was stirred for overnight. After completion of the starting material 1,4-dioxane was removed under reduced pressure to get a solid material. The obtained solid was washed with ethyl acetate and dried thoroughly to obtain the target material (4) as a white solid (3.7 g, 99.19%). Compound 4 was taken forward to the next step without purification.

Procedure for Compound 5:

Compound 4 (1.5 g, 4.0 mmol) as its hydrochloride salt was taken in acetonitrile (30 mL) and $K_2CO_3$ (1.32 g, 8.0 mmol, 2 eq.) was added to it at room temperature. Chloroacetyl chloride (0.81 g, 6.0 mmol, 1.5 eq.) was added to the reaction mixture slowly at 0° C., and the reaction was warmed to room temperature overnight. The reaction was monitored by TLC and after its completion, the reaction was quenched with water and reaction mixture was extracted with ethyl acetate (2×25 mL). The combined organic layers were washed with brine and water and dried over sodium sulfate. The solvent was evaporated and the compound (5) purified by re-crystallization (hexane) to afford the title compound as a white solid (1.6 g, 94.67%).

1-(4-(Naphthalen-2-ylsulfonyl)piperazin-1-yl)-2-(p-tolylthio)ethanone

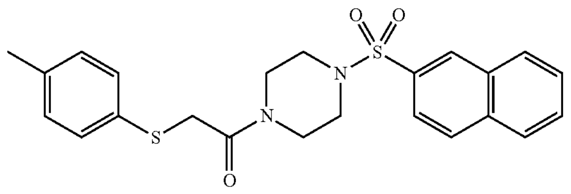

Thio phenol (100 mg, 0.85 mmol), 2-chloro-1-(4-(naphthalen-2-ylsulfonyl)piperazin-1-yl)ethanone (compound 5, 0.3 g, 0.85 mmol) and anhydrous potassium carbonate (0.293 g, 2.125 mmol) were stirred for over night in dry acetonitrile (20 mL). The mixture was then stirred into a large volume of water and the solution extracted with ether. Unreacted phenol was removed with cold 1N NaOH solution. The ether extract was dried over anhydrous sodium sulphate, filtered and concentrated under reduced pressure. The crude material was purified by column chromatography to yield the title compound in quantitative yield.

$^1$HNMR (DMSO-d6, 500 MHz): 2.18 (s, 3H), 2.91-3.02 (m, 4H), 3.52-3.62 (m, 4H), 3.82 (s, 2H), 6.85 (d, 2H), 7.02 (d, 2H), 7.73-7.79 (m, 3H), 8.13 (d, 1H), 8.21 (m, 2H), 8.44 (s, 1H). MS (ESI): 441.1 (M+1).

2-(2,4-Dichlorophenoxy)-1-(4-(naphthalen-2-ylsulfonyl)piperazin-1-yl)ethanone

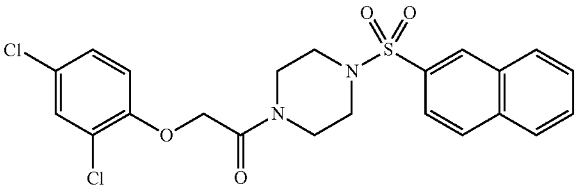 [SMILES: O=C(COc1ccc(Cl)cc1Cl)N1CCN(S(=O)(=O)c2ccc3ccccc3c2)CC1]

2,4-dichloro phenol (138 mg, 0.85 mmol), 2-chloro-1-(4-(naphthalen-2-ylsulfonyl)piperazin-1-yl)ethanone (compound 5, 0.3 g, 0.85 mmol) and anhydrous potassium carbonate (0.293 g, 2.125 mmol) were stirred for over night in dry acetonitrile (20 mL). The mixture was poured into a large volume of water and the solution extracted with diethyl ether. Un-reacted phenol was removed with cold 1N NaOH solution. The ether extract was dried over anhydrous sodium sulphate, filtered and concentrated under reduced pressure. The crude material was purified by column chromatography to yield the title compound (350 mg, 87.5% yield) as an off-white solid.

$^1$HNMR (DMSO-d6, 500 MHz): 2.94-3.04 (m, 4H), 3.52-3.58 (m, 4H), 3.91 (s, 2H), 6.95 (d, 1H), 7.21 (d, 1H), 7.40 (s, 1H), 7.73-7.79 (m, 3H), 8.13 (d, 1H), 8.21 (dd, 2H), 8.43 (s, 1H). MS (ESI): 479.2 (M+).

2-(4-fluorophenoxy)-1-(4-(naphthalen-2-ylsulfonyl)piperazin-1-yl)ethanone

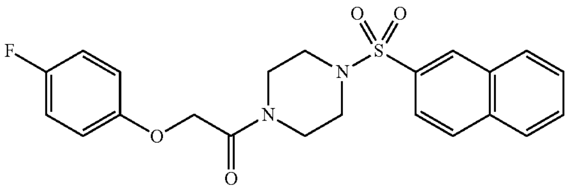 [SMILES: O=C(COc1ccc(F)cc1)N1CCN(S(=O)(=O)c2ccc3ccccc3c2)CC1]

4-fluoro phenol (95.32 mg, 0.85 mmol), 2-chloro-1-(4-(naphthalen-2-ylsulfonyl)piperazin-1-yl)ethanone (compound 5, 0.3 g, 0.85 mmol) and anhydrous potassium carbonate (0.293 g, 2.125 mmol) were stirred for over night in dry acetonitrile (20 mL). The mixture was poured into a large volume of water and the solution extracted with ether. Un-reacted phenol was removed with cold 1N NaOH solution. The ether extract was dried over anhydrous sodium sulphate, filtered and concentrated under reduced pressure. The crude material was purified by column chromatography to yield the title compound (340 mg, 94.44% yield) as an off-white solid.

$^1$HNMR (DMSO-d6, 500 MHz): 2.91-3.02 (m, 4H), 3.52-3.59 (m, 4H), 4.77 (s, 2H), 6.81 (d, 2H), 6.98 (d, 2H), 7.71-7.79 (m, 3H), 8.11 (d, 1H), 8.21 (dd, 2H), 8.42 (s, 1H). MS (ESI): 429.2 (M+1).

2-(Benzyloxy)-1-(4-(naphthalen-2-ylsulfonyl)piperazin-1-yl)ethanone

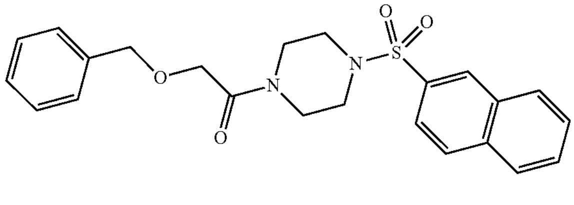 [SMILES: O=C(COCc1ccccc1)N1CCN(S(=O)(=O)c2ccc3ccccc3c2)CC1]

To a suspension of sodium hydride (35.88 mg, 60 percent in oil) in dry THF (20 mL) cooled to 0° C. under nitrogen atmosphere, a solution of benzylalcohol (0.09 g, 0.717 mmol) in THF (1 mL) was added drop wise to the mixture over 25 minutes, and the mixture was brought to room temperature and stirred for 2 h. The reaction was again cooled to 0° C., to which a solution of 2-chloro-1-(4-(naphthalen-2-ylsulfonyl)piperazin-1-yl)ethanone (compound 5) in THF (20 mL) was added drop wise over 30 minutes. After being stirred for over night at room temperature, the reaction mixture was poured into ice cold water and extracted with ethyl acetate (2×10 mL). The organic layer was washed with brine solution and then dried over anhydrous sodium sulfate, and the solvent was distilled off under reduced pressure. The resultant crude product was purified by column chromatography on silica gel (hexane:ethyl acetate:1:1) to obtain the title product (60 mg, 24%) as an off-white solid.

$^1$HNMR (DMSO-d6, 500 MHz): 2.96 (m, 4H), 3.48-3.57 (m, 4H), 4.11 (s, 2H), 4.39 (s, 2H), 7.21 (m, 5H), 7.72-7.78 (m, 3H), 8.12 (d, 1H), 8.21 (dd, 2H), 8.41 (s, 1H). MS (ESI): 425.2 (M+1).

2-(2,4-Difluorophenoxy)-1-(4-(naphthalen-2-ylsulfonyl)piperazin-1-yl)ethanone

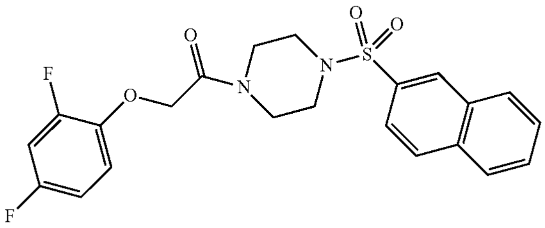 [SMILES: O=C(COc1ccc(F)cc1F)N1CCN(S(=O)(=O)c2ccc3ccccc3c2)CC1]

2,4-difluoro phenol (110 mg, 0.85 mmol), 2-chloro-1-(4-(naphthalen-2-ylsulfonyl)piperazin-1-yl)ethanone (compound 5, 0.3 g, 0.85 mmol) and anhydrous potassium carbonate (0.352 g, 2.55 mmol) were stirred for over night in dry acetonitrile (20 mL). The mixture was poured into a large volume of water and the solution extracted with ether. Unreacted phenol was removed with cold 1N NaOH solution. The ether extract was dried over anhydrous sodium sulphate, filtered and concentrated under reduced pressure. The crude material was purified by re-crystallization to yield the title compound (280 mg, 73.87% yield) as an off-white solid.

$^1$HNMR (DMSO-d6, 500 MHz): 2.97-3.04 (m, 4H), 3.52-3.58 (m, 4H), 4.82 (s, 2H), 6.84 (m, 1H), 6.98 (m, 1H), 7.15 (m, 1H), 7.68-7.78 (m, 3H), 8.11 (d, 1H), 8.21 (dd, 2H), 8.41 (s, 1H). MS (ESI): 447.1 (M+1).

1-(4-(Naphthalen-2-ylsulfonyl)piperazin-1-yl)-2-(pyridin-3-yloxy)ethanone

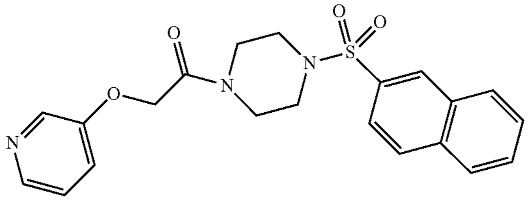 [SMILES: O=C(COc1cccnc1)N1CCN(S(=O)(=O)c2ccc3ccccc3c2)CC1]

3-hydroxy pyridine (97 mg, 1.02 mmol), 2-chloro-1-(4-(naphthalen-2-ylsulfonyl)piperazin-1-yl)ethanone (compound 5, 0.3 g, 0.85 mmol) and anhydrous potassium carbonate (0.352 g, 2.55 mmol) were stirred for over night in dry acetonitrile (20 mL). The mixture was poured into a large volume of water and the solution extracted with ether. Unreacted phenol was removed with cold 1N NaOH solution. The ether extract was dried over anhydrous sodium sulphate, filtered and concentrated under reduced pressure. The crude material was purified by re-crystallization to yield the title compound (40 mg, 11.46% yield) as an off-white solid. 60% of the un-reacted starting material was also recovered from the reaction.

$^1$HNMR (DMSO-d6, 500 MHz): 3.04 (m, 4H), 3.56 (m, 4H), 4.84 (s, 2H), 7.22 (m, 2H), 7.72-7.81 (m, 3H), 8.11 (m, 2H), 8.21 (m, 3H), 8.16 (s, 1H). MS (ESI): 412.2 (M+1).

1-(4-(Naphthalen-2-ylsulfonyl)piperazin-1-yl)-2-(phenylamino)ethanone

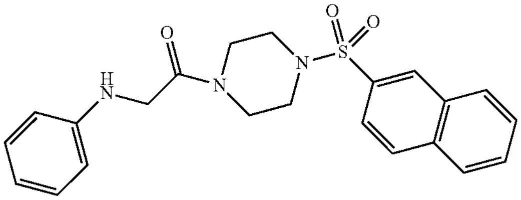 [SMILES: O=C(CNc1ccccc1)N1CCN(S(=O)(=O)c2ccc3ccccc3c2)CC1]

A stirred solution of aniline (15.3 g, 0.16 mol) and diisopropyl ethylamine (DIEA, 56 mL, 0.33 mol) in acetonitrile (120 mL) is heated to 60° C. and 2-chloro-1-(4-(naphthalen-2-ylsulfonyl)piperazin-1-yl)ethanone (compound 5, 0.3 g, 0.85 mmol) is added dropwise. The reaction mixture is kept stirring at this temperature for another 3 h and is then evaporated to dryness. Water is added to the residue, and extracted with ethyl acetate (2×30 mL). The organic extract was dried over anhydrous sodium sulphate, filtered and concentrated under reduced pressure. The resultant crude product was purified by column chromatography on silica gel (hexane:ethyl acetate:3:7) to obtain the title compound (300 mg, 76.53%) as an off-white solid.

$^1$HNMR (DMSO-d6, 500 MHz): 2.98 (m, 4H), 3.58 (m, 4H), 3.81 (s, 2H), 6.44 (t, 1H), 6.53 (d, 2H), 6.98 (m, 2H), 7.68-7.78 (m, 3H), 8.11 (d, 1H), 8.21 (dd, 2H), 8.42 (s, 1H). MS (ESI): 410.2 (M+1).

2-(Methylamino)-1-(4-(naphthalen-2-ylsulfonyl)piperazin-1-yl)ethanone

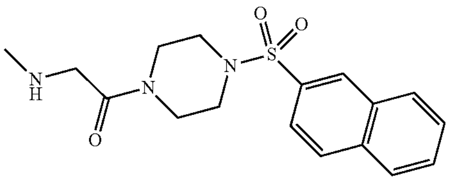 [SMILES: CNCC(=O)N1CCN(S(=O)(=O)c2ccc3ccccc3c2)CC1]

To a stirred solution of 2-chloro-1-(4-(naphthalen-2-ylsulfonyl)piperazin-1-yl)ethanone (compound 5, 0.1 g, 0.85 mmol) in THF (10 mL) diisopropyl ethyl amine (81 mg, 0.62 mmol) was added at 0° C. followed by methyl amine solution (30% solution, 10 mL). The reaction mixture was allowed to stir for overnight at room temperature. The reaction mixture was poured into a large volume of water (50 mL) and the solution was extracted with ethyl acetate. The combined organic extract was dried over anhydrous sodium sulphate, filtered and concentrated under reduced pressure. The crude material was purified by column chromatography to obtain the title compound (20.0 mg, 22.90% yield) as an off-white solid.

$^1$HNMR ($CDCl_3$, 500 MHz): 2.52 (s, 3H), 3.14 (m, 4H), 3.46 (m, 2H), 3.58 (s, 2H), 3.72 (m, 2H), 7.62-7.76 (m, 3H), 7.97 (d, 1H), 8.01 (dd, 2H), 8.37 (s, 1H). MS (ESI): 348.1 (M+1).

2-(4-fluorophenylthio)-1-(4-(naphthalen-2-ylsulfonyl)piperazin-1-yl)ethanone

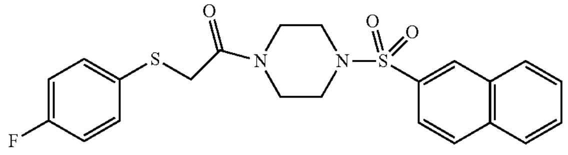 [SMILES: O=C(CSc1ccc(F)cc1)N1CCN(S(=O)(=O)c2ccc3ccccc3c2)CC1]

$^1$HNMR (DMSO-d6, 500 MHz): 2.89-2.98 (m, 4H), 3.57 (m, 4H), 3.86 (s, 2H), 6.98 (t, 2H), 7.22 (m, 2H), 7.72-7.79 (m, 3H), 8.12 (d, 1H), 8.20 (dd, 2H), 8.44 (s, 1H). MS (ESI): 445.1 (M+1).

2-(2-methoxyphenoxy)-1-(4-(naphthalen-2-ylsulfonyl)piperazin-1-yl)ethanone

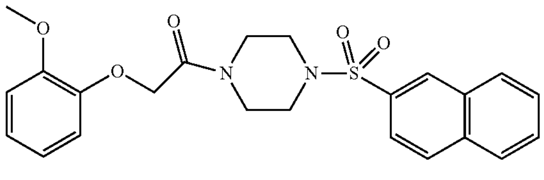 [SMILES: COc1ccccc1OCC(=O)N1CCN(S(=O)(=O)c2ccc3ccccc3c2)CC1]

For this synthesis, a similar procedure was followed as above except 2-methoxy phenol was utilized instead of 2,4-dichlorophenol.

$^1$HNMR (DMSO-d6, 500 MHz): 2.98 (m, 4H), 3.57 (m, 4H), 3.63 (s, 3H), 4.67 (s, 2H), 6.69-6.84 (m, 4H), 7.71-7.79 (m, 3H), 8.12 (d, 1H), 8.20 (dd, 2H), 8.44 (s, 1H). MS (ESI): 441.2 (M+1).

3-(2-(4-(naphthalen-2-ylsulfonyl)piperazin-1-yl)-2-oxoethoxy)benzonitrile

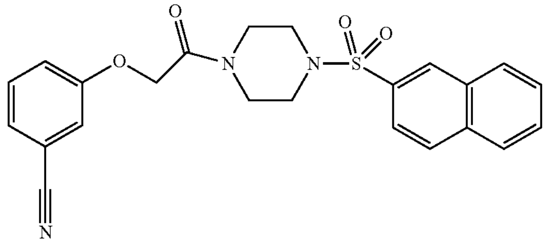 [SMILES: N#Cc1cccc(OCC(=O)N2CCN(S(=O)(=O)c3ccc4ccccc4c3)CC2)c1]

$^1$HNMR (DMSO-d6, 500 MHz): 2.98-3.04 (m, 4H), 3.56 (m, 4H), 4.83 (s, 2H), 7.19 (dd, 1H), 7.36 (m, 3H), 7.77 (m, 3H), 8.12 (d, 1H), 8.20 (dd, 2H), 8.45 (s, 1H). MS (ESI): 436.2 (M+1).

Scheme 3:

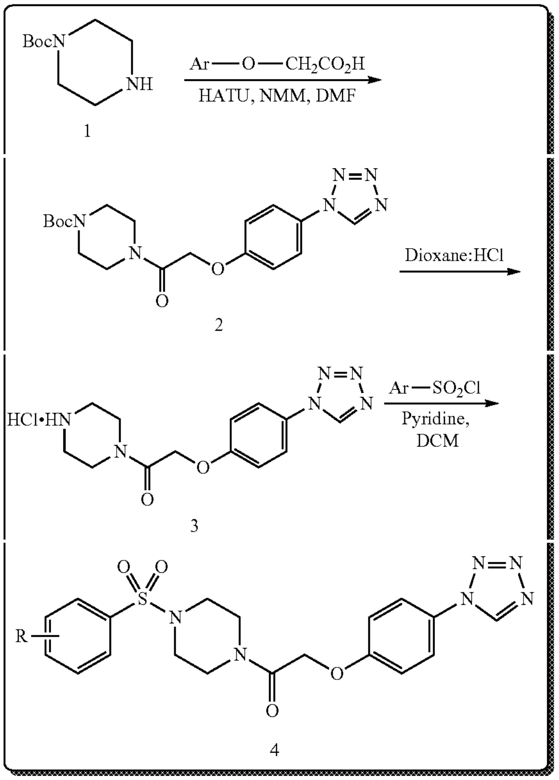

1

2

3

4

Procedure for Compound 2:

In a two neck round bottom flask, tert-butyl-piperazine-1-carboxylate (17.0 mmoles, 3.25 g, 1.1 eq) (1) and 2-(4-(1H-tetrazol-1-yl)phenoxy)acetic acid (15.0 mmoles, 3.5 g, 1 eq) were charged in DCM (70 mL). DIPEA (10.27 g, 75 mmoles, 5 eq) and HATU (12.0 g, 30.0 mmoles, 2 eq) were added to the reaction mixture. The resulting mixture was stirred at room temperature for overnight. After completion of the reaction, water (10 mL) was added and extracted with DCM (2×30 mL). The combined organic layers were dried over anhydrous $Na_2SO_4$, filtered and concentrated under reduced pressure. The crude product (2) was purified by column chromatography to obtain the title compound (4.8 g, 77.79%) as a white solid.

Procedure for Compound 3:

In a two neck round bottom flask with tert-butyl-4-(2-(4-(1H-tetrazol-1-yl)phenoxy)acetyl)piperazine-1-carboxylate (3, 12.0 mmoles, 4.8 g, 1 eq) in it, 1,4-dioxane-HCl (20% sol, 50 mL) was added. The resulting mixture was stirred for overnight. After complete consumption of the starting material, 1,4-dioxane was removed under reduced pressure and a crude solid product was obtained. The crude material (3) was washed with hexane and dried well to obtain the target material (0.32 g, 95%) as a light yellow solid.

2-(4-(1H-tetrazol-1-yl)phenoxy)-1-(4-(naphthalen-2-ylsulfonyl)piperazin-1-yl)ethanone

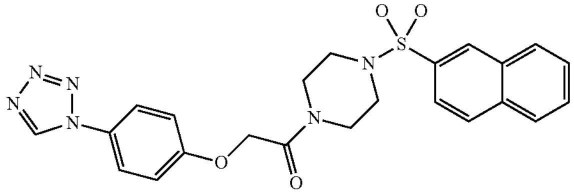 [SMILES: O=C(COc1ccc(-n2cnnn2)cc1)N1CCN(S(O)(O)c2ccc3ccccc3c2)CC1]

In a two neck round bottom flask 2-(4-(1H-tetrazol-1-yl)phenoxy)-1-(piperazine-1-yl)ethanone hydrochloride (compound 3, 0.882 mmoles, 0.286 g, 1 eq) and 2-naphthalene sulfonylchloride (0.882 mmoles, 0.2 g, 1 eq) were charged in DCM (20 mL). TEA (2.646 moles, 0.267 g, 3 eq) was added drop wise to the reaction mixture over a period of 10 min at 0° C. The resulting mixture was stirred for 3 h at room temperature and monitored by TLC. After completion of the reaction, water (10 mL) was added and extracted with DCM (2×20 mL). The combined organic layers were washed with brine (1×20 mL), dried over anhydrous $Na_2SO_4$ and concentrated under reduced pressure. The crude product was purified by column chromatography (Silica gel 60-120, 3:7, Ethyl acetate/Hexane) to obtain the title compound (0.300 g, 71.09%) as an off-white solid.

$^1$HNMR ($CDCl_3$, 500 MHz): 3.08 (m, 4H), 3.54 (m, 4H), 4.69 (s, 2H), 6.99 (d, 2H), 7.41 (d, 2H), 7.42-7.51 (m, 3H), 7.85 (d, 1H), 7.98 (m, 2H), 8.29 (s, 2H), 8.79 (s, 1H). MS (ESI): 479.1 (M+1).

2-(4-(1H-tetrazol-1-yl)phenoxy)-1-(4-(naphthalen-1-ylsulfonyl)piperazin-1-yl)ethanone

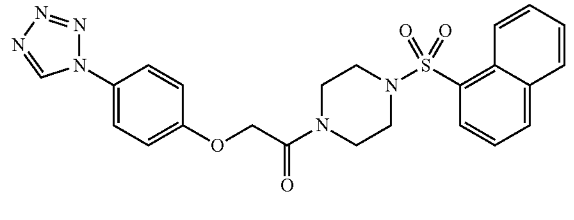 [SMILES: O=C(COc1ccc(-n2cnnn2)cc1)N1CCN(S(=O)(=O)c2cccc3ccccc23)CC1]

In a two neck round bottom flask, 2-(4-(1H-tetrazol-1-yl)phenoxy)-1-(piperazine-1-yl)ethanone hydrochloride (compound 3, 0.882 mmoles, 0.286 g, 1 eq) and 1-naphthalene sulfonylchloride (0.882 mmoles, 0.2 g, 1 eq) were charged in DCM (20 mL). TEA (2.646 moles, 0.267 g, 3 eq) was added drop wise to the reaction mixture over a period of 10 min at 0° C. The resulting mixture was stirred for 3 h at room temperature and monitored by TLC. After completion of the reaction, water (10 mL) was added and extracted with DCM (2×20 mL). The combined organic layers were washed with brine (1×20 mL), dried over anhydrous $Na_2SO_4$ and concentrated under reduced pressure. The crude product was purified by column chromatography (Silica gel 60-120, 3:7, Ethyl acetate/Hexane) to obtain the title compound (0.300 g, 71.09%) as off-white solid.

$^1$HNMR (DMSO-d6, 500 MHz): 3.03-3.19 (m, 4H), 3.51 (m, 4H), 4.87 (s, 2H), 7.03 (d, 2H), 7.71-7.79 (m, 5H), 8.16 (dd, 2H), 8.35 (d, 1H), 8.71 (d, 1H), 9.97 (s, 1H). MS (ESI): 479.2 (M+1).

2-(4-(1H-tetrazol-1-yl)phenoxy)-1-(4-(quinolin-8-ylsulfonyl)piperazin-1-yl)ethanone

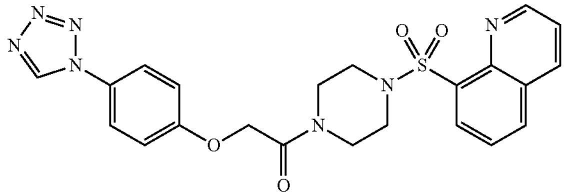 [SMILES: O=C(COc1ccc(-n2cnnn2)cc1)N1CCN(S(=O)(=O)c2cccc3cccnc23)CC1]

The synthesis of the title compound was done following a similar procedure outlined above except the sulfonyl chloride taken here is 8-quinoline sulfonylchloride (1.3 mmoles, 0.3 g, 1 eq) instead of 1-napthalene sulfonyl chloride. The crude product was purified by washing with ether and n-Hexane to obtain the title compound (0.250 g, 39.68%) as an off-white solid.

$^1$HNMR (DMSO-d6, 500 MHz): 3.33-3.41 (m, 4H), 3.51 (m, 4H), 4.91 (s, 2H), 7.09 (d, 2H), 7.71-7.81 (m, 4H), 8.33 (d, 2H), 8.40 (d, 1H), 8.58 (d, 1H), 9.09 (d, 1H), 9.97 (s, 1H). MS (ESI): 480.2 (M+1).

2-(4-(1H-tetrazol-1-yl)phenoxy)-1-(4-(5-chloro-2-methoxyphenylsulfonyl)piperazin-1-yl)ethanone

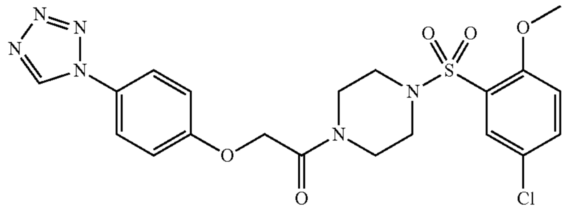 [SMILES: COc1ccc(Cl)cc1S(=O)(=O)N1CCN(C(=O)COc2ccc(-n3cnnn3)cc2)CC1]

The synthesis of the title compound was done following a similar procedure as outlined above except the sulfonyl chloride taken here is 2-methoxy-5-chloro benzene sulfonyl chloride (0.9 mmoles, 0.22 g,) instead of 1-napthalene sulfonyl chloride. The crude product was purified by washing with ether and n-Hexane to obtain the title compound (0.250 g 55.55%) as an off-white solid.

$^1$HNMR (DMSO-d6, 500 MHz): 3.18-3.21 (m, 4H), 3.51 (m, 4H), 3.92 (s, 3H), 4.98 (s, 2H), 7.15 (d, 2H), 7.32 (d, 1H), 7.72 (m, 2H), 7.78 (d, 2H), 9.98 (s, 1H). MS (ESI): 493.0 (M+1).

2-(4-(1H-tetrazol-1-yl)phenoxy)-1-(4-(phenylsulfonyl)piperazin-1-yl)ethanone

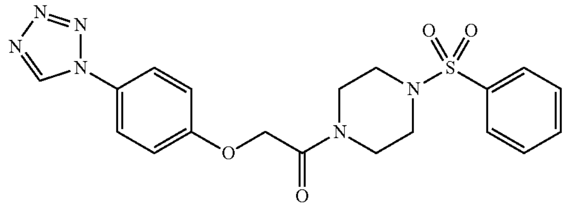 [SMILES: O=C(COc1ccc(-n2cnnn2)cc1)N1CCN(S(=O)(=O)c2ccccc2)CC1]

The synthesis of the title compound was carried out following a similar procedure as outlined above except the sulfonyl chloride taken here is benzene sulfonylchloride (0.9 mmoles, 0.163 g, 1 eq) instead of 1-napthalene sulfonyl chloride, benzene sulfonylchloride (0.9 mmoles, 0.163 g, 1 eq). The crude product was purified by washing with ether and n-Hexane to obtain the title compound (0.290 g 73.23%) as off-white solid.

$^1$HNMR (DMSO-d6, 500 MHz): 2.95 (m, 4H), 3.57 (m, 4H), 4.96 (s, 2H), 7.12 (d, 2H), 7.64-7.78 (m, 1H), 9.97 (s, 1H). MS (ESI): 429.0 (M+1).

2-(4-(1H-tetrazol-1-yl)phenoxy)-1-(4-(4-fluorophenylsulfonyl)piperazin-1-yl)ethanone

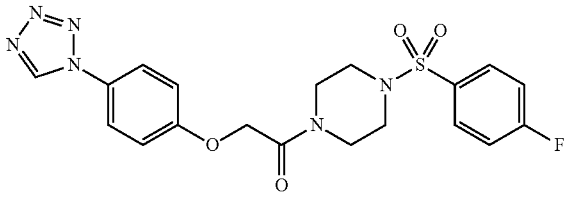 [SMILES: O=C(COc1ccc(-n2cnnn2)cc1)N1CCN(S(=O)(=O)c2ccc(F)cc2)CC1]

The synthesis of the title compound was carried out following a similar procedure as outlined above except the sulfonyl chloride taken here is 4-fluoro benzene sulfonyl chloride (0.9 mmoles, 0.180 g) instead of 1-napthalene sulfonyl chloride. The crude product was purified by washing with ether and n-Hexane to obtain the title compound (0.280 g 67.96%) as off-white solid.

$^1$HNMR (DMSO-d6, 500 MHz): 2.95 (m, 4H), 3.56 (m, 4H), 4.89 (s, 2H), 7.08 (d, 2H), 7.43 (m, 2H), 7.73 (m, 2H), 7.81 (m, 2H), 9.87 (s, 1H). MS (ESI): 447.1 (M+1).

2-(4-(1H-tetrazol-1-yl)phenoxy)-1-(4-(2,6-difluorophenylsulfonyl)piperazin-1-yl)ethanone

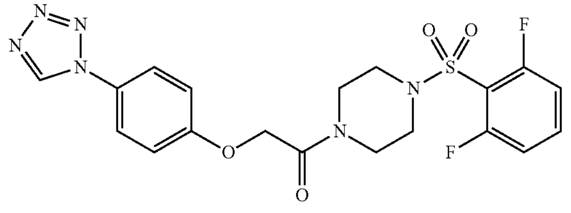 [SMILES: O=C(COc1ccc(-n2cnnn2)cc1)N1CCN(S(=O)(=O)c2c(F)cccc2F)CC1]

The synthesis of the title compound was carried out following a similar procedure as outlined above except the sulfonyl chloride taken here is 2,6-difluoro benzene sulfonylchloride (0.9 mmoles, 0.196 g, 1 eq) instead of 1-napthalene sulfonyl chloride. The crude product was purified by washing with ether and n-Hexane to obtain the title compound (0.220 g 52.38%) as off-white solid.

$^1$HNMR (DMSO-d6, 500 MHz): 3.12-3.22 (m, 4H), 3.40 (m, 4H), 4.96 (s, 2H), 7.12 (d, 2H), 7.37 (t, 2H), 7.77 (d, 2H), 7.79 (m, 1H), 9.97 (s, 1H). MS (ESI): 447.1 (M+1).

6-(4-(2-(4-(1H-tetrazol-1-yl)phenoxy)acetyl)piperazin-1-ylsulfonyl)-3,5-dimethyl benzo[d]oxazol-2(3H)-one

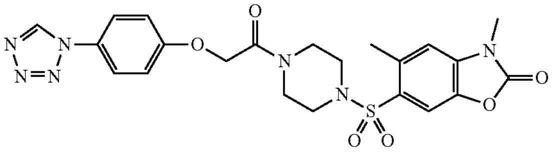 [SMILES: Cc1cc2c(cc1S(=O)(=O)N1CCN(C(=O)COc3ccc(-n4cnnn4)cc3)CC1)oc(=O)n2C]

The synthesis of the title compound was carried out following a similar procedure as outlined above except the sulfonyl chloride taken here is 3,5-dimethyl-2-oxo-2,3-dihydrobenzo[d]oxazole-6-sulfonyl chloride (0.9 mmoles, 0.22 g) instead of 1-napthalene sulfonyl chloride. The crude product was purified by washing with ether and n-hexane to obtain the title compound (0.08 g 48.0%) as off-white solid.

$^1$HNMR (DMSO-d6, 500 MHz): 2.62 (s, 3H), 3.06-3.18 (m, 4H), 3.39 (s, 3H), 3.56 (m, 4H), 4.96 (s, 2H), 7.17 (d, 2H), 7.40 (s, 1H), 7.72 (s, 1H), 7.79 (d, 2H). MS (ESI): 514.1 (M+1).

Scheme 4:

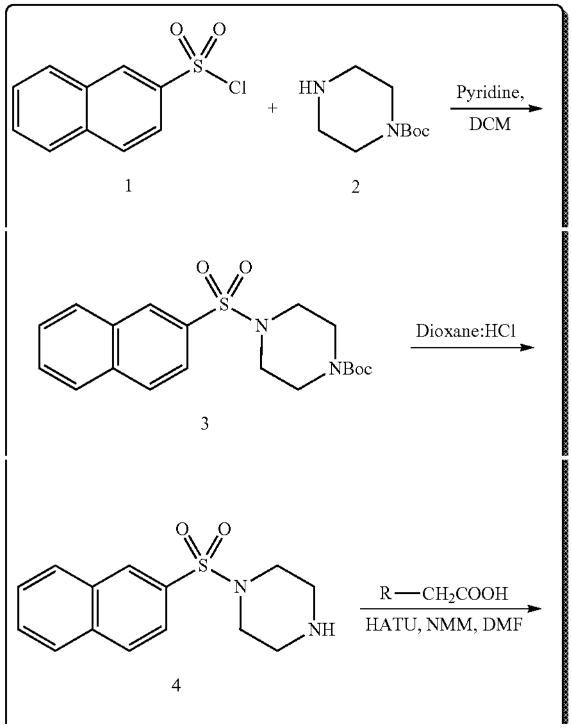

-continued

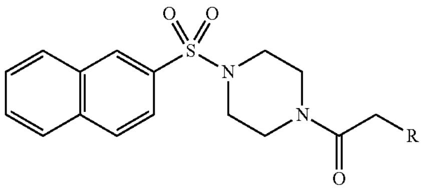

5

General Procedure for Compound 3:

In a two neck round bottom flask, tert-butyl-piperazine-1-carboxylate (2) (5.3680 moles, 1.000 g) and 2-Naphthalene sulfonyl chloride (1) (5.905 moles, 1.338 g) were charged in DCM (20 mL). Pyridine (13.417 moles, 1.08 mL) was added slowly at room temperature. The resulting mixture was stirred for 3 h at room temperature. After completion of the reaction, dilute HCl was added (10 mL) and extracted with DCM (2×20 mL). The combined organic layers were washed with water (15 mL) and brine solution (1×20 mL). The resulting organic layer was dried over anhydrous $Na_2SO_4$ and concentrated under reduced pressure. The crude product (3) was obtained as a white solid (1.800 g, 89.10%).

General Procedure for Compound 4:

In a two neck round bottom flask tert-butyl-4-(2-(4-(naphthalene-2-ylsulfonyl) piperazine-1-carboxylate (3) (0.0047 moles, 1.800 g) was taken and 1,4-dioxane-HCl (30 mL) was added to it. The resulting mixture was stirred for overnight. After complete consumption of the starting material as indicated by TLC, 1,4-dioxane was removed under reduced pressure and a solid material was obtained. The crude material (4) was washed with ethyl acetate and dried well to obtain the target material as white solid (1.400 g, 93.95%).

1-(4-(naphthalen-2-ylsulfonyl)piperazin-1-yl)-2-phenoxyethanone

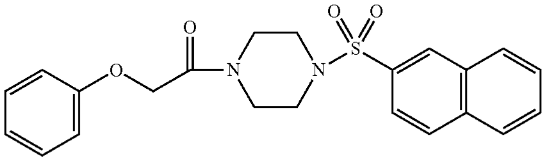 [SMILES: O=C(COc1ccccc1)N1CCN(S(=O)(=O)c2ccc3ccccc3c2)CC1]

In a two neck round bottom flask, 1-(naphthalene-2-ylsulfonyl)piperazine hydrochloride (compound 4, 0.639 moles, 0.200 g) and 2-phenoxyacetylchloride (0.639 moles, 0.109 g) were charged in DCM (20 mL). TEA (2.557 moles, 0.258 g) was added slowly to the reaction flask. The resulting mixture was stirred for 3 h at room temperature. After completion of the reaction, water (10 mL) was added and extracted with DCM (2×20 mL). The combined organic layers were washed with brine (1×20 mL), dried over $Na_2SO_4$ and concentrated under reduced pressure. The crude product was purified by column chromatography (Silica gel 60-120, 4:6, Ethyl acetate/Hexane) to obtain the title compound (0.200 g, 76.33%).

$^1$HNMR (DMSO-d6, 500 MHz): 2.95 (m, 4H), 3.57 (m, 4H), 4.72 (s, 2H), 6.80 (m, 3H), 7.15 (m, 2H), 7.75 (m, 3H), 8.09 (d, 1H), 8.20 (m, 2H), 8.42 (s, 1H). MS (ESI): 411.1 (M+1).

Benzyl 4-(naphthalen-2-ylsulfonyl)piperazine-1-carboxylate

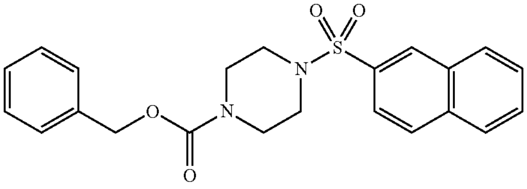 [SMILES: O=C(OCc1ccccc1)N1CCN(S(=O)(=O)c2ccc3ccccc3c2)CC1]

In a two neck round bottom flask, 1-(naphthalene-2-ylsulfonyl)piperazine hydrochloride (compound 4, 0.72 mmoles, 0.200 g) and pyridine (7.22 mmoles, 2 mL) were charged in DCM (20 mL) at 0° C. CBZCl (1.08 mmoles, 0.30 g) was added slowly at the same temperature and then allowed the reaction mixture to stir for 3 h at room temperature. After completion of the reaction, water (10 mL) was added and extracted with DCM (2×20 mL). The combined organic layers were washed with brine (1×20 mL), dried over $Na_2SO_4$ and concentrated under reduced pressure. The crude product was purified by Column Chromatography (Silica gel 60-120, MeOH/DCM) to obtain the title compound (0.150 g, 50.6%) as an off-white solid.

$^1$HNMR (DMSO-d6, 500 MHz): 2.95 (m, 4H), 3.51 (m, 4H), 4.99 (s, 2H), 7.24 (m, 4H), 7.74 (m, 3H), 8.09 (d, 1H), 8.20 (m, 2H), 8.42 (s, 1H). MS (ESI): 423.2 (M+Na).

1-(4-(Naphthalen-2-ylsulfonyl)piperazin-1-yl)-2-(p-tolyloxy)ethanone

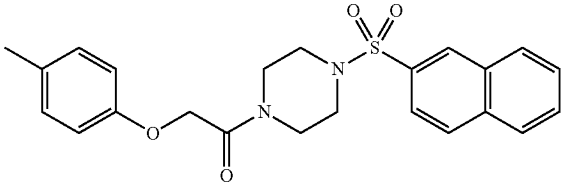 [SMILES: Cc1ccc(OCC(=O)N2CCN(S(=O)(=O)c3ccc4ccccc4c3)CC2)cc1]

To a stirred solution of 2-chloro-1-(4-(naphthalen-2-ylsulfonyl)piperazin-1-yl)ethanone (compound 4, 0.2 g, 0.64 mmol) and 2-(p-tolyloxy)acetic acid (106 mg, 0.64 mmol) in dry DCM (20 mL), DIPEA (495 mg, 3.86 mmol) followed by HATU (486 mg, 1.27 mmol) was added at room temperature and stirred overnight. The mixture was then diluted with DCM and washed with water (2×10 mL) & brine (2×10 mL). The organic extract was dried over anhydrous sodium sulphate, filtered and concentrated under reduced pressure. The crude material was purified by column chromatography to yield the title compound (0.21 g, 77.5%) as an off-white solid.

$^1$HNMR (DMSO-d6, 500 MHz): 2.16 (s, 3H), 2.95-3.04 (m, 4H), 3.57 (m, 4H), 4.63 (s, 2H), 6.65 (d, 2H), 6.92 (d, 2H), 7.73-7.79 (m, 3H), 8.11 (d, 1H), 8.21 (dd, 2H), 8.42 (s, 1H). MS (ESI): 424.1 (M+1).

Methyl 4-(2-(4-(naphthalen-2-ylsulfonyl)piperazin-1-yl)-2-oxoethoxy)benzoate

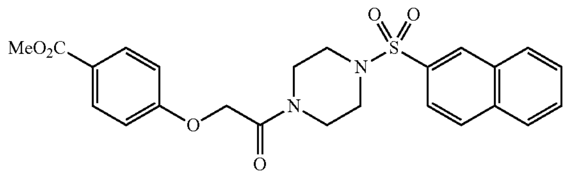 [SMILES: COC(=O)c1ccc(OCC(=O)N2CCN(S(=O)(=O)c3ccc4ccccc4c3)CC2)cc1]

To a stirred solution of 2-chloro-1-(4-(naphthalen-2-yl-sulfonyl)piperazin-1-yl)ethanone (compound 4, 0.2 g, 0.64 mmol) and 2-(4-(methoxycarbonyl)phenoxy)acetic acid (134 mg, 0.64 mmol) taken in dry DCM (20 mL), DIPEA (495 mg, 3.86 mmol) followed by HATU (486 mg, 1.27 mmol) was added at room temperature and stirred overnight. The mixture was then diluted with DCM washed with water (2×10 mL) and brine (2×10 mL) The organic extract was dried over anhydrous sodium sulphate, filtered and concentrated under reduced pressure. The crude material was purified by column chromatography to yield the title compound (0.189 g, 63.21%) as an off-white solid.

$^1$HNMR (DMSO-d6, 500 MHz): 2.95-3.04 (m, 4H), 3.57 (m, 4H), 3.89 (s, 3H), 4.86 (s, 2H), 6.92 (d, 2H), 7.71-7.81 (m, 3H), 8.11 (d, 1H), 8.21 (dd, 2H), 8.42 (s, 1H). MS (ESI): 424.1 (M+1).

1-(4-(Naphthalen-2-ylsulfonyl)piperazin-1-yl)-3-phenylpropan-1-one

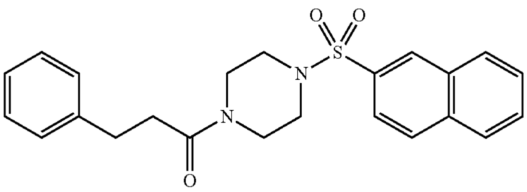 [SMILES: O=C(CCc1ccccc1)N1CCN(S(=O)(=O)c2ccc3ccccc3c2)CC1]

To a stirred solution of 2-chloro-1-(4-(naphthalen-2-ylsulfonyl)piperazin-1-yl)ethanone (compound 4, 0.208 g, 0.66 mmol) and 3-phenylpropanoic acid (100 mg, 0.66 mmol) taken in dry DCM (30 mL), DIPEA (430 mg, 3.32 mmol) followed by HATU (504 mg, 1.33 mmol) was added at room temperature and stirred overnight. The mixture was then diluted with DCM washed with water (2×10 mL) & brine (2×10 mL). The organic extract was dried over anhydrous sodium sulphate, filtered and concentrated under reduced pressure. The crude material was purified by column chromatography to yield the title compound (0.225 g, 82.72%) as solid.

$^1$HNMR (DMSO-d6, 500 MHz): 2.95-3.04 (m, 4H), 3.57 (m, 4H), 3.89 (s, 3H), 4.86 (s, 2H), 6.92 (d, 2H), 7.71-7.81 (m, 3H), 8.11 (d, 1H), 8.21 (dd, 2H), 8.42 (s, 1H). MS (ESI): 424.1 (M+1).

1-(4-(Naphthalen-2-ylsulfonyl)piperazin-1-yl)-3-(4-(trifluoromethyl)phenyl) propan-1-one

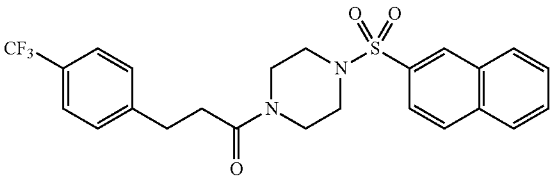 [SMILES: O=C(CCc1ccc(C(F)(F)F)cc1)N1CCN(S(=O)(=O)c2ccc3ccccc3c2)CC1]

To a stirred solution of 2-chloro-1-(4-(naphthalen-2-ylsulfonyl)piperazin-1-yl)ethanone (compound 4, 0.086 g, 0.27 mmol) and 3-(4-(trifluoromethyl)phenyl)propanoic acid (60 mg, 0.27 mmol) taken in dry DCM (20 mL), DIPEA (72 mg, 1.37 mmol) followed by HATU (208 mg, 0.55 mmol) was added at room temperature and stirred overnight. The mixture was then diluted with DCM washed with water (2×10 mL) & brine (2×10 mL). The organic extract was dried over anhydrous sodium sulphate, filtered and concentrated under reduced pressure. The crude material was purified by column chromatography to yield the title compound (0.118 g, 90.07%) as solid.

$^1$HNMR (DMSO-d6, 500 MHz): 2.60 (t, 2H), 2.79 (t, 2H), 2.96 (m, 4H), 3.55 (m, 4H), 7.38 (d, 2H), 7.55 (d, 2H), 7.77 (m, 3H), 8.09 (d, 1H), 8.20 (dd, 2H), 8.42 (s, 1H). MS (ESI): 477.2 (M+1).

Pyridin-3-ylmethyl 4-(naphthalen-2-ylsulfonyl)piperazine-1-carboxylate

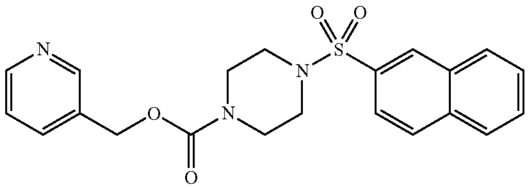 [SMILES: O=C(OCc1cccnc1)N1CCN(S(=O)(=O)c2ccc3ccccc3c2)CC1]

To a stirred solution of 2-chloro-1-(4-(naphthalen-2-ylsulfonyl)piperazin-1-yl)ethanone (compound 4, 0.250 g, 0.905 mmol) and pyridin-3-yl-methanol (98 mg, 0.905 mmol) taken in dry DCM (10 mL), triphosgene (294 mg, 0.99 mmol) was added at 0° C. and allowed to stir at room temperature for 3 h. The mixture was then diluted with DCM washed with water (2×10 mL) & brine (2×10 mL). The organic extract was dried over anhydrous sodium sulphate, filtered and concentrated under reduced pressure. The crude material was purified by column chromatography to yield the title compound (0.109 g, 30.27%) as a solid.

$^1$HNMR (DMSO-d6, 500 MHz): 2.98 (m, 4H), 3.51 (m, 4H), 5.01 (s, 2H), 7.32 (m, 1H), 7.71-7.79 (m, 4H), 8.11 (d, 1H), 8.21 (dd, 2H), 8.42 (s, 1H), 8.45 (d, 1H), 8.12 (s, 1H). MS (ESI): 412.1 (M+1).

(4-(naphthalen-2-ylsulfonyl)piperazin-1-yl)(2-(4-(trifluoromethyl)phenyl)cyclopropyl)methanone

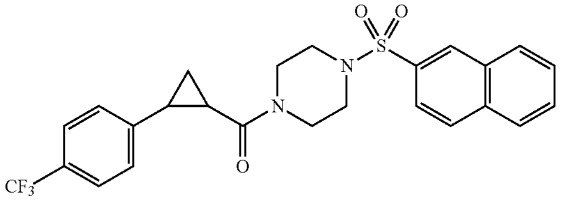 [SMILES: O=C(C1CC1c1ccc(C(F)(F)F)cc1)N1CCN(S(=O)(=O)c2ccc3ccccc3c2)CC1]

To a stirred solution of 2-chloro-1-(4-(naphthalen-2-ylsulfonyl)piperazin-1-yl)ethanone (compound 4, 0.086 g, 0.27 mmol) and 3-(4-(trifluoromethyl)phenyl)propanoic acid (60 mg, 0.27 mmol) in dry DCM (20 mL), DIPEA (72 mg, 1.37 mmol) followed by HATU (208 mg, 0.55 mmol) was added at room temperature and stirred overnight. The mixture was then diluted with DCM washed with water (2×10 mL) & brine (2×10 mL). The organic extract was dried over anhydrous sodium sulphate, filtered and concentrated under reduced pressure. The crude material was purified by column chromatography to yield the title compound AGI-604 (0.118 g, 90.07%) as solid.

$^1$HNMR (DMSO-d6, 500 MHz): 1.21 (m, 1H), 1.36 (m, 1H), 2.35 (m, 2H), 2.95-3.04 (m, 4H), 3.53-3.78 (m, 4H), 7.33 (d, 2H), 7.58 (d, 2H), 7.50-7.59 (m, 3H), 8.11 (d, 1H), 8.20 (dd, 2H), 8.42 (s, 1H). MS (ESI): 489.1 (M+1).

Scheme 5:

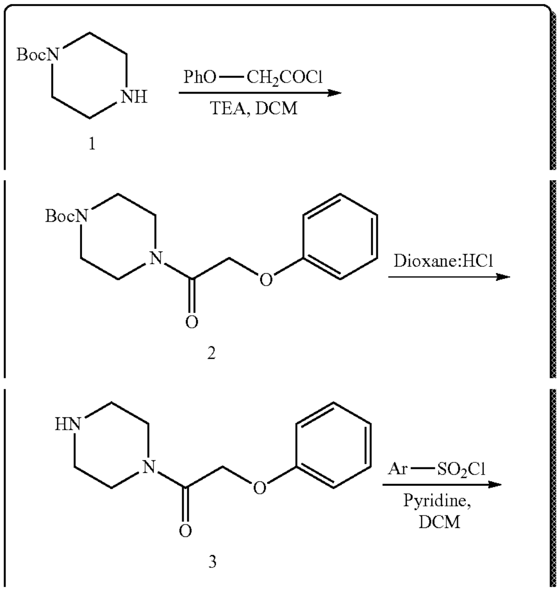

1

2

3

-continued

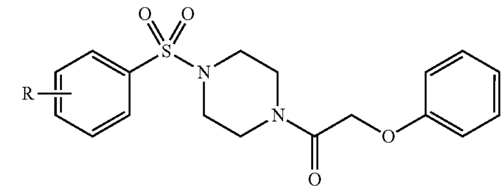

4

Procedure for Compound 2:

In a two neck round bottom flask, 1-tert-butyl piperazine-1-carboxylate (1) (0.0106 moles, 2.0 g) and 2-phenoxyacetylchloride (0.0118 moles, 2.0 g) were charged in DCM (30 mL). TEA (0.0322 moles, 3.25 g) was added slowly to the reaction container at 0° C. The resulting mixture was stirred for 3 h at room temperature. After completion of the reaction, water (10 mL) was added and extracted with DCM (2×50 mL). The combined organic layers were washed with brine (2×20 mL), dried over $Na_2SO_4$ and concentrated under reduced pressure. The crude product was purified by column chromatography (Silica gel 60-120, 6:4, Ethyl acetate/Hexane) to obtain the target molecule (2) (3.1 g, 90.37%).

Procedure for Compound 3:

In a two neck round bottom flask tert-butyl 4-(2-phenoxyacetyl)piperazine-1-carboxylate (2) (9.6 mmoles, 3.1 g) was taken and 1,4-dioxane-HCl (20% sol, 30 mL) was added to it. The resulting mixture was stirred for overnight. After completion of the reaction as indicated by TLC, 1,4-dioxane was removed under reduced pressure and a solid material was obtained. The crude material was washed with hexane and dried thoroughly to obtain the target material (3) (2.4 g, 96.77%) as light yellow solid.

General Procedure for the Sulfonamides Preparation:

In a two neck round bottom flask, 4-phenoxy-1-(piperazine-1-yl)ethanone hydrochloride (1 eq) and aryl sulfonylchloride (1 eq) were charged in DCM (10 mL). TEA (3 eq) was added drop wise over a period of 10 min at 0° C. The resulting mixture was stirred for 3 h at room temperature. After completion of the reaction, water (10 mL) was added and extracted with DCM (2×20 mL). The combined organic layers were washed with brine (1×20 mL), dried over anhydrous $Na_2SO_4$ and concentrated under reduced pressure. The crude product was purified by column chromatography (Silica gel 60-120, Ethyl acetate/Hexane) to obtain the target molecule.

2-Phenoxy-1-(4-(phenylsulfonyl)piperazin-1-yl)ethanone

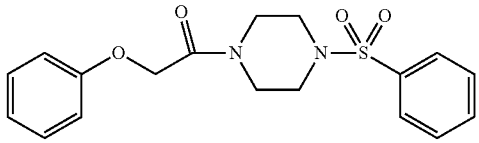 [SMILES: O=C(COc1ccccc1)N1CCN(S(=O)(=O)c2ccccc2)CC1]

$^1$HNMR (DMSO-d6, 500 MHz): 2.87-3.01 (m, 4H), 3.56 (m, 4H), 4.78 (s, 2H), 6.84 (d, 2H), 6.92 (m, 1H), 7.23 (t, 2H), 7.68 (m, 2H), 7.77 (m, 3H). MS (ESI): 361.0 (M+1).

1-(4-(5-chloro-2-methoxyphenylsulfonyl)piperazin-1-yl)-2-phenoxyethanone

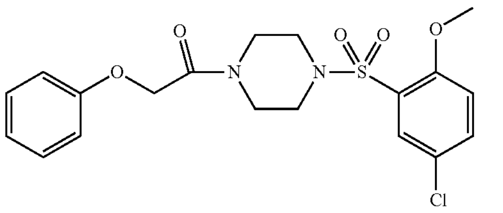 [SMILES: COc1ccc(Cl)cc1S(=O)(=O)N1CCN(C(=O)COc2ccccc2)CC1]

$^1$HNMR (DMSO-d6, 500 MHz): 3.11-3.21 (m, 4H), 3.52 (m, 4H), 3.91 (s, 3H), 4.80 (s, 2H), 6.88-6.93 (m, 3H), 7.23-7.34 (m, 3H), 7.71 (s, 1H), 7.75 (d, 1H). MS (ESI): 425.0 (M+1).

1-(4-(4-fluorophenylsulfonyl)piperazin-1-yl)-2-phenoxyethanone

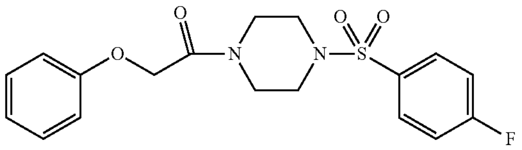 [SMILES: O=C(COc1ccccc1)N1CCN(S(=O)(=O)c2ccc(F)cc2)CC1]

$^1$HNMR (DMSO-d6, 500 MHz): 2.83-2.97 (m, 4H), 3.56 (m, 4H), 4.78 (s, 2H), 6.83 (d, 2H), 6.91 (t, 1H), 7.22 (m, 2H), 7.54 (m, 2H), 7.81 (m, 2H). MS (ESI): 379.1 (M+1).

1-(4-(3,5-dimethylphenylsulfonyl)piperazin-1-yl)-2-phenoxyethanone

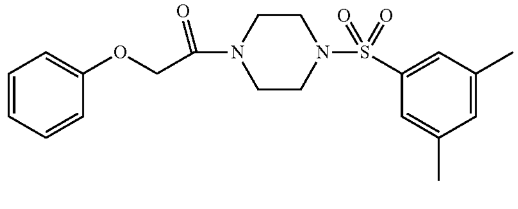 [SMILES: Cc1cc(C)cc(S(=O)(=O)N2CCN(C(=O)COc3ccccc3)CC2)c1]

$^1$HNMR (DMSO-d6, 500 MHz): 2.39 (s, 6H), 2.83-2.95 (m, 4H), 3.56 (m, 4H), 4.78 (s, 2H), 6.83 (d, 2H), 6.91 (m, 1H), 7.22 (t, 2H), 7.36 (s, 2H), 7.39 (s, 1H). MS (ESI): 389.1 (M+1).

1-(4-(benzo[d][1,3]dioxol-5-ylsulfonyl)piperazin-1-yl)-2-phenoxyethanone

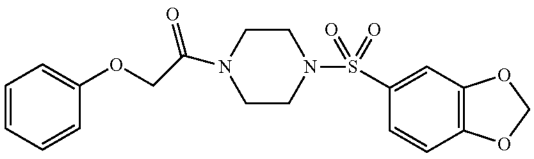 [SMILES: O=C(COc1ccccc1)N1CCN(S(=O)(=O)c2ccc3c(c2)OCO3)CC1]

$^1$HNMR (DMSO-d6, 500 MHz): 2.83-2.95 (m, 4H), 3.56 (m, 4H), 4.78 (s, 2H), 6.20 (s, 2H), 6.85 (d, 2H), 6.91 (m, 1H), 7.18 (d, 1H), 7.21-7.28 (m, 4H). MS (ESI): 405.1 (M+1).

3,5-dimethyl-6-(4-(2-phenoxyacetyl)piperazin-1-ylsulfonyl)benzo[d]oxazol-2(3H)-one

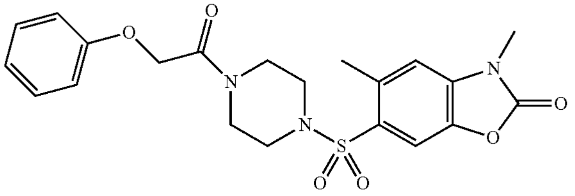 [SMILES: Cc1cc2c(cc1S(=O)(=O)N1CCN(C(=O)COc3ccccc3)CC1)oc(=O)n2C]

$^1$HNMR (DMSO-d6, 500 MHz): 2.62 (s, 3H), 3.01-3.13 (m, 4H), 3.39 (s, 3H), 3.57 (m, 4H), 4.79 (s, 2H), 6.87-6.72 (m, 3H), 7.24 (m, 2H), 7.40 (s, 1H), 7.71 (s, 1H). MS (ESI): 446.1 (M+1).

1-(4-(benzo[d]thiazol-6-ylsulfonyl)piperazin-1-yl)-2-phenoxyethanone

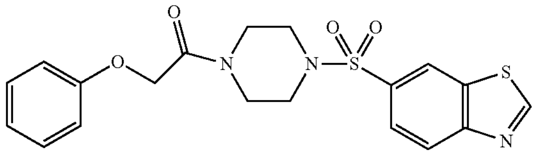 [SMILES: O=C(COc1ccccc1)N1CCN(S(=O)(=O)c2ccc3ncsc3c2)CC1]

$^1$HNMR (DMSO-d6, 500 MHz): 2.97-3.01 (m, 4H), 3.58 (m, 4H), 4.78 (s, 2H), 6.80-6.84 (m, 3H), 7.19 (t, 2H), 7.85 (d, 1H), 8.33 (d, 1H), 8.73 (s, 1H), 9.71 (s, 1H). MS (ESI): 419.1 (M+1).

1-(4-(2,3-dihydrobenzo[b][1,4]dioxin-6-ylsulfonyl)piperazin-1-yl)-2-phenoxy ethanone

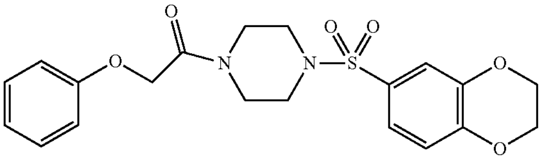 [SMILES: O=C(COc1ccccc1)N1CCN(S(=O)(=O)c2ccc3c(c2)OCCO3)CC1]

$^1$HNMR (DMSO-d6, 500 MHz): 2.84-2.97 (m, 4H), 3.58 (m, 4H), 4.34 (m, 4H), 4.79 (s, 2H), 6.86-6.72 (m, 3H), 7.12 (d, 1H), 7.18-7.26 (m, 4H). MS (ESI): 419.1 (M+1).

1-((2S,6R)-2,6-dimethyl-4-(napthalen-2-ylsulfonyl)piperazin-1-yl)-2-phenoxy ethanone

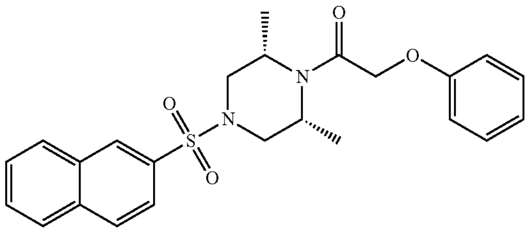 [SMILES: C[C@@H]1CN(S(=O)(=O)c2ccc3ccccc3c2)C[C@H](C)N1C(=O)COc1ccccc1]

In a two neck round bottom flask (3S,5R)-3,5-dimethyl-1-(naphthalen-2-yl-sulfonyl)piperazine (100 mg, 0.33 moles) was dissolved in 25 mL of acetonitrile. $K_2CO_3$ (71 mg, 0.53 moles) was added to the reaction flask at room temperature under nitrogen atmosphere and allowed the reaction mixture to stir for about 10 min. The flask was then cooled to 0° C. and phenoxy acetyl chloride (83 μl, 0.49 moles) was added to the reaction flask drop wise at the same temperature. After addition, the reaction mixture was slowly warmed to room temperature and allowed it to stir for 3 hr. TLC indicated complete consumption of the starting material. The reaction was quenched with cold water (25 mL) and extracted with ethyl acetate (2×25 mL). The combined organic phase was washed with brine solution and dried over sodium sulphate. Solvent was removed under reduced pressure to give crude material which was purified by column chromatography (20% ethyl acetate and hexane) to afford the title compound with 98% purity.

$^1$HNMR (DMSO-d6: 500 MHz): 1.25 (s, 3H), 1.3 (s, 3H), 2.2 (t, 2H), 3.6 (s 2H), 4.1 (t, 1H), 4.2 (d, 1H), 4.3 (d, 1H), 4.4 (d, 1H), 7.21 (m, 5H), 7.72-7.78 (m, 3H), 8.12 (d, 1H), 8.21 (dd, 2H), 8.41 (s, 1H). MS: (ESI): 439.54 (M+1). HPLC: 98.06%

1-((2S,6R)-2,6-dimethyl-4-(napthalen-2-ylsulfonyl) piperazin-1-yl)-2-(2-methoxy phenoxy)ethanone

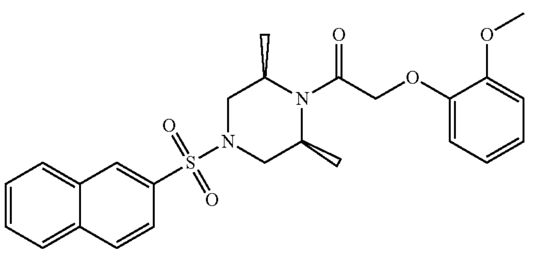 [SMILES: COc1ccccc1OCC(=O)N1[C@H](C)CN(S(=O)(=O)c2ccc3ccccc3c2)C[C@@H]1C]

2-Chloro-1-((2S,6R)-2,6-dimethyl-4-(naphthalene-2-yl-sulfonyl)piperazin-1-yl)ethanone (200 mg, 0.52 moles) was dissolved in 20 mL of acetonitrile. Dry $K_2CO_3$ (106 mg, 0.79 moles) was added to the reaction mixture under nitrogen atmosphere and allowed to stir for about ten minutes. 2-methoxyphenol (97 mg, 0.78 moles) was slowly added to the reaction at room temperature and allowed the reaction to continue for another 4 h. The reaction was monitored by TLC and after product formation was observed, the reaction mixture was diluted with cold water (10 mL) and extracted with ethyl acetate (25 mL×2). The combined organic layers were washed with bicarbonate followed by brine & then dried over sodium sulphate. The solvent was evaporated on reduced pressure to afford crude product which was purified by column chromatography to yield the title compound as an off-white solid.

$^1$HNMR (DMSO-d6: 500 MHz): 1.25 (s, 3H), 1.3 (s, 3H), 2.2 (t, 2H), 3.6 (s, 2H), 4.1 (t, 1H), 3.9 (s, 3h), 4.2 (d, 1H), 4.3 (d, 1H), δ4.4 (d, 1H), 7.21 (m, 5H), 7.72-7.78 (m, 3H), 8.12 (d, 1H). MS: (ESI): 468.57 (M+1). HPLC: 90.08%

N-(1-(2-Phenoxyacetyl)piperidin-4-yl) naphthalene-2-sulfonamide

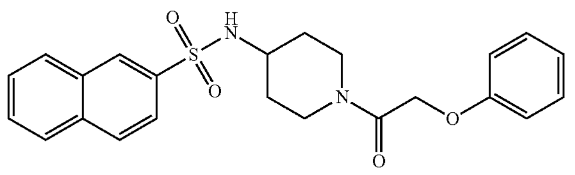 [SMILES: O=C(COc1ccccc1)N1CCC(NS(=O)(=O)c2ccc3ccccc3c2)CC1]

N-(Piperidin-4-yl)naphthalene-2-sulfonamide (50 mg, 0.17 moles) was dissolved in 10 mL DCM and to that di-isopropyl ethyl amine (0.1 mL, 0.34 moles) was added under nitrogen at 0° C. The reaction was allowed to stir for 10 min and phenoxy acetyl chloride (33 mg, 0.19 moles) was added at 0° C. and warmed room temperature and stirred for 3 h. After completion of the reaction as monitored by TLC, reaction was quenched with cold water and extracted with ethyl acetate (2×25 mL). The combined organic phase was washed with bicarbonate solution and brine and dried over sodium sulphate. The solvent was filtered and evaporated on rotavap to obtain a crude compound which was washed further with hexane to yield the title compound as a white solid.

$^1$HNMR (DMSO-d6: 500 MHz): 1.85 (m, 2H), 1.86 (m, 2H), 2.2 (t, 1H), 3.0 (t, 1H), 3.2 (s, 2H), 3.1 (d, 1H), 4.0 (d, 1H), 4.9 (m, 1H), 7.21 (m, 5H), 7.72-7.78 (m, 3H), 8.12 (d, 1H), 8.21 (dd, 2H), 8.41 (s, 1H). MS: (ESI): 424.51 (M+1). HPLC: 91.08%

N-(1-(2-Phenoxyacetyl)piperidin-4-yl)methyl)naphthalene-2-sulfonamide

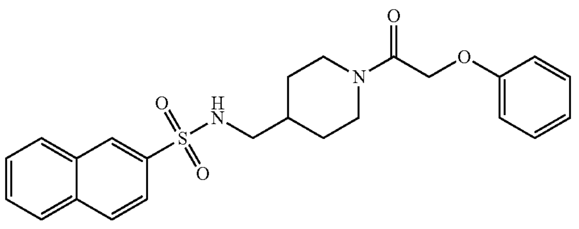 [SMILES: O=C(COc1ccccc1)N1CCC(CNS(=O)(=O)c2ccc3ccccc3c2)CC1]

In a two neck round bottom flask, N-(Piperidin-4-ylmethyl)naphthalene-2-sulfonamide (50 mg, 0.16 mmol) was dissolved in 20 mL of DCM under nitrogen atmosphere and di-isopropyl ethyl amine (0.05 mL, 0.33 mmol) was added at 0° C. The reaction was stirred for 10 min at the same temperature and phenoxy acetyl chloride (17 mg, 0.099 mmol) was slowly added. The reaction was warmed to room temperature and allowed it to stir for 3 h. After completion of the reaction, the reaction was quenched with water and extracted with ethyl acetate (2×25 mL). The combined organic phase was washed with bicarbonate solution and brine and dried over sodium sulphate. The solvent was filtered and evaporated on rotavap to obtain a crude compound which was washed twice with pentane dried over high vacuum to yield the title compound as a white solid.

$^1$HNMR (DMSO-d6: 500 MHz): 1.0 (d, 1H), 1.1 (d, 1H), 1.3 (d, 1H), 1.9 (d, 2H), 2.3 (s, 2H), 3.0 (t, 1H), 3.9 (d, 1H), 4.2

(d, 1H), 4.9 (s, 2H), 7.21 (m, 5H), 7.72-7.78 (m, 3H), 8.12 (d, 1H), 8.21 (dd, 2H), 8.41 (s, 1H). MS: (ESI): 439.54 (M+1). HPLC: 97.4%

3,5-Dimethyl-6-(4-2-(p-tolyloxy)acetyl)piperazin-1-ylsulfonyl)benzo[d]oxazol-2(3H)-one

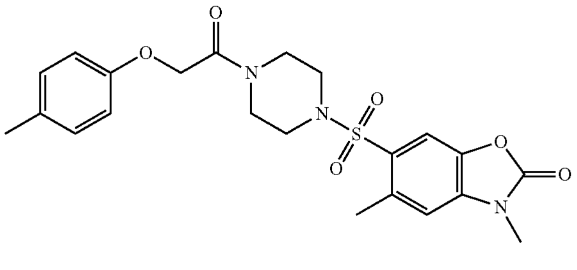 [SMILES: Cc1ccc(OCC(=O)N2CCN(S(=O)(=O)c3cc4oc(=O)n(C)c4cc3C)CC2)cc1]

3,5-Dimethyl-6-(piperazin-1-ylsulfonyl)benzo[d]oxazol-2(3H)-one was dissolved in 25 mL dry DCM and to that di-isopropyl ethyl amine (0.1 mL, 0.64 mmol) and HATU (182 mg, 0.48 mmol) was added at 0° C. under $N_2$ atmosphere. The reaction mixture was stirred for 10 min and 2-(p-tolyloxy)acetic acid (64 mg, 0.384 mmol) was slowly added. The reaction was warmed to room temperature and allowed it to stir for 12 h. After completion of the reaction, the reaction was quenched with water and extracted with ethyl acetate (2×25 mL). The combined organic phase was washed with bicarbonate solution and brine and dried over sodium sulphate. The solvent was filtered and evaporated on rotavap to obtain a crude compound which was purified by column chromatography to yield pure title compound as a white solid.

$^1$HNMR (DMSO-d6: 500 MHz): 2.2 (s, 3H), 2.6 (s, 2H), 3.1 (d, 2H), 3.1 (s, 2H), 3.6 (s, 2H), 3.7 (m, 4H), 4.9 (s, 2H), 6.9 (dd, 2H), 7.0 (dd, 2H), 7.4 (s, 1H), 7.6 (s, 1H). MS: (ESI): 460.01 (M+1). HPLC: 93.1%

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A compound of formula (II) or a pharmaceutically acceptable salt thereof, wherein:

(II)

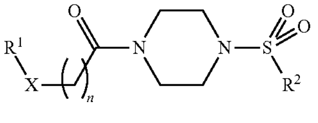

n is 1 or 2;

X is O, S, $NR^b$, or cycloalkylenyl;

$R^1$ is selected from optionally substituted alkyl, optionally substituted aryl, optionally substituted heteroaryl, optionally substituted heterocyclyl, optionally substituted cycloalkyl, an optionally substituted aralkyl, and optionally substituted heteroaralkyl;

$R^2$ is an optionally substituted quinolinyl; and $R^b$ is hydrogen or alkyl.

2. The compound of claim 1, wherein the compound is of formula (II-a):

(II-a)

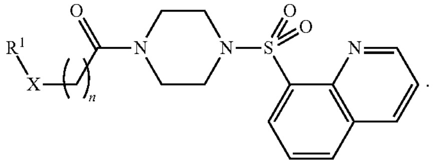

3. A compound of formula (III) or a pharmaceutically acceptable salt thereof, wherein:

(III)

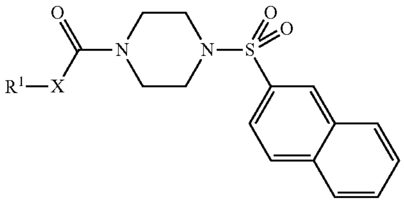

when X is S, or cycloalkylenyl, $R^1$ is selected from substituted alkyl, substituted aryl, optionally substituted heteroaryl, optionally substituted heterocyclyl, optionally substituted cycloalkyl, optionally substituted aralkyl, and optionally substituted heteroaralkyl; and when X is O, $R^1$ is selected from optionally substituted aralkyl and optionally substituted heteroaralkyl.

4. A pharmaceutical composition comprising a compound of any one of claims 1 to 3.

5. A method of activating PKM2 in a subject, the method comprising administering to said subject a pharmaceutical composition comprising a compound of formula (II) or pharmaceutically acceptable salt thereof, wherein:

(II)

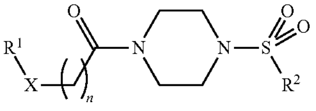

n is 1 or 2;

X is O, S, $NR^b$, or cycloalkylenyl;

$R^1$ is selected from optionally substituted alkyl, optionally substituted aryl, optionally substituted heteroaryl, optionally substituted heterocyclyl, optionally substituted cycloalkyl, an optionally substituted aralkyl, and optionally substituted heteroaralkyl;

$R^2$ is a bicyclic heteroaryl; and $R^b$ is hydrogen or alkyl.

6. A compound of formula (I) or a pharmaceutically acceptable salt thereof, wherein:

(I)

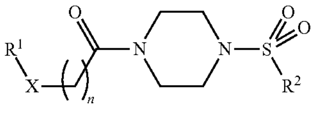

n is 1 or 2;

X is S, $NR^b$, alkylenyl, cycloalkylenyl, or a bond;

$R^1$ is unsubstituted aryl;

$R^2$ is unsubstituted aryl; and $R^b$ is hydrogen or alkyl.

7. The compound of claim 6, wherein n is 1.

8. The compound of claim 6, wherein n is 2.

9. The compound of claim 6, wherein X is $NR^b$.

10. The compound of claim 6, wherein X is alkylenyl or a bond.

11. The compound of claim 6, wherein the compound is selected from the following:

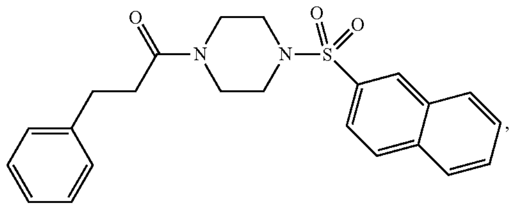 [SMILES: O=C(CCc1ccccc1)N1CCN(S(=O)(=O)c2ccc3ccccc3c2)CC1]

,

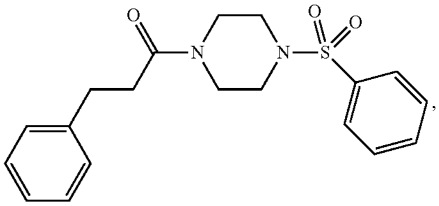

, and

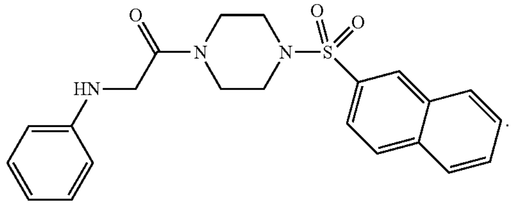 [SMILES: O=C(COc1ccccc1)N1CCN(S(=O)(=O)c2ccc3ccccc3c2)CC1]

.

12. The compound of claim 6, wherein the compound has the following structure:

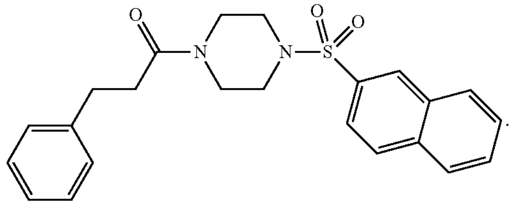

.

13. A pharmaceutical composition comprising a compound of any one of claims 6-12.

14. A method of activating PKM2 in a subject, the method comprising administering to said subject a pharmaceutical composition comprising a compound of formula (I) or a pharmaceutically acceptable salt thereof, wherein:

(I)

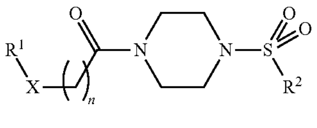

n is 1 or 2;

X is O, S, $NR^b$, alkylenyl, cycloalkylenyl, or a bond;

$R^1$ is unsubstituted aryl;

$R^2$ is unsubstituted aryl; and $R^b$ is hydrogen or alkyl.

15. A method of activating PKM2 in a subject, the method comprising administering to said subject a pharmaceutical composition comprising a compound of formula (III) or a pharmaceutically acceptable salt thereof, wherein:

(III)

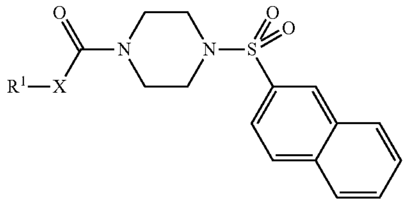

when X is S, or cycloalkylenyl, $R^1$ is selected from optionally substituted alkyl, optionally substituted aryl, optionally substituted heteroaryl, optionally substituted heterocyclyl, optionally substituted cycloalkyl, optionally substituted aralkyl, and optionally substituted heteroaralkyl; and when X is O, $R^1$ is selected from optionally substituted aralkyl and optionally substituted heteroaralkyl.

16. A compound of formula (I) or a pharmaceutically acceptable salt thereof, wherein:

(I)

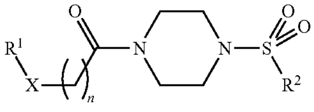

n is 1 or 2;

X is O, S, $NR^b$, alkylenyl, cycloalkylenyl, or a bond;

$R^1$ is unsubstituted aryl;

$R^2$ is unsubstituted naphthyl; and $R^b$ is hydrogen or alkyl.

17. The compound of claim 16, wherein n is 1.

18. The compound of claim 16, wherein n is 2.

19. The compound of claim 16, wherein X is O or $NR^b$.

20. The compound of claim 16, wherein X is alkylenyl or a bond.

21. The compound of claim 16, wherein the compound is

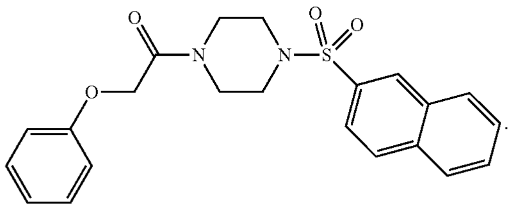

.

22. The compound of claim 1, wherein the compound is

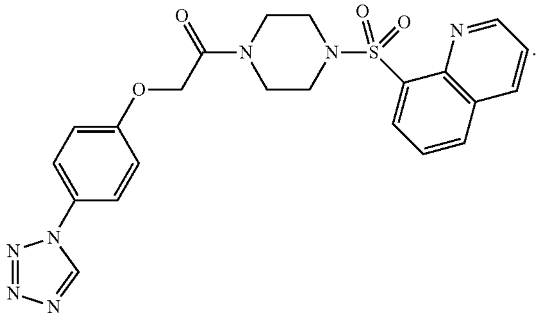 [SMILES: O=C(COc1ccc(-n2cnnn2)cc1)N1CCN(S(=O)(=O)c2cccc3cccnc23)CC1]

.

23. A compound selected from the following:
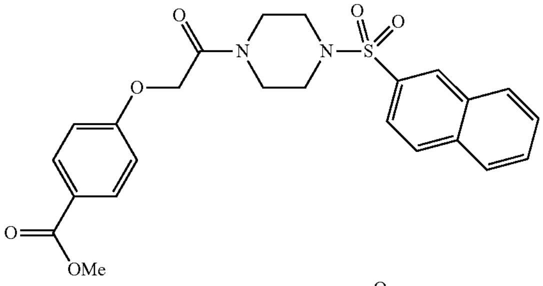
, or
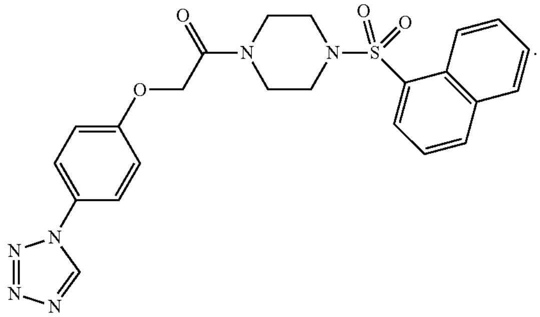
.
24. The compound of claim 16, wherein the compound is
"
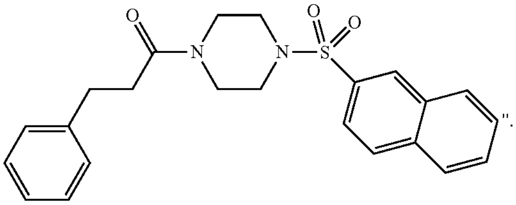
".
25. The compound of claim 16, wherein the compound is
"
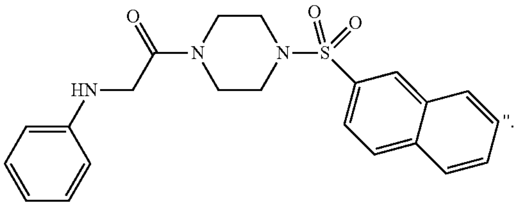
".
26. The compound of claim 22, wherein the compound is
"
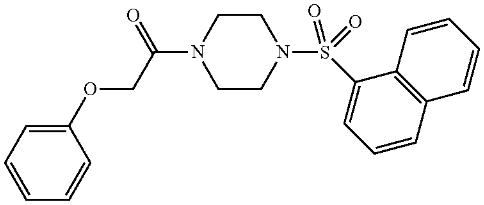
".
27. The compound of claim 16, wherein the compound is
"
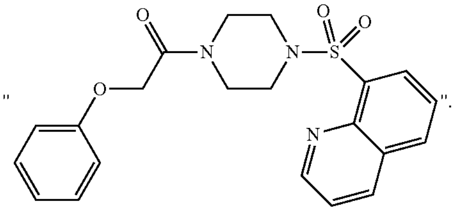 [SMILES: O=C(COc1ccccc1)N1CCN(S(=O)(=O)c2cccc3cccnc23)CC1]
".
* * * * *